US005792886A

United States Patent [19]
Sabahi et al.

[11] Patent Number: 5,792,886
[45] Date of Patent: Aug. 11, 1998

[54] PRODUCTION OF RACEMIC 2-(6-METHOXY-2-NAPHTHYL) PROPIONIC ACID OF PRECURSORS THEREOF

[75] Inventors: Mahmood Sabahi; Kevin J. Theriot, both of Baton Rouge; Brian F. Becnel, Port Allen, all of La.

[73] Assignee: Albemarle Corporation, Richmond, Va.

[21] Appl. No.: 780,309

[22] Filed: Jan. 8, 1997

[51] Int. Cl.$^6$ .................................................. C07C 62/06
[52] U.S. Cl. .................... 562/466; 568/628; 568/632; 260/665 G; 260/665 R
[58] Field of Search ................ 562/466; 568/628, 568/632; 260/665 G, 665 R

[56] References Cited

U.S. PATENT DOCUMENTS

| | | | |
|---|---|---|---|
| 3,159,649 | 12/1964 | Brown et al. | 260/343.3 |
| 3,228,831 | 1/1966 | Nicholson et al. | 167/53 |
| 3,385,886 | 5/1968 | Nicholson et al. | 260/515 |
| 3,562,336 | 2/1971 | Nelson | 260/613 |
| 3,600,437 | 8/1971 | Marshall | 260/520 |
| 3,626,012 | 12/1971 | Fried et al. | 260/599 |
| 3,637,767 | 1/1972 | Alvarez | 260/348 R |
| 3,641,127 | 2/1972 | Farge et al. | 260/516 |
| 3,651,106 | 3/1972 | Harrison | 260/429 R |
| 3,651,148 | 3/1972 | Nelson | 260/606.5 B |
| 3,651,149 | 3/1972 | Harrison | 260/606.5 B |
| 3,652,683 | 3/1972 | Harrison | 260/612 D |
| 3,658,858 | 4/1972 | Harrison | 260/429 R |
| 3,658,863 | 4/1972 | Harrison | 260/438.1 |
| 3,663,584 | 5/1972 | Alvarez | 260/429.9 |
| 3,663,713 | 5/1972 | Fried et al. | 424/333 |
| 3,681,432 | 8/1972 | Nelson | 260/473 F |
| 3,683,015 | 8/1972 | Dyson | 260/520 |
| 3,686,183 | 8/1972 | Dyson | 260/284 |
| 3,694,476 | 9/1972 | Alvarez | 260/429 R |
| 3,720,708 | 3/1973 | Halpern | 260/519 |
| 3,755,427 | 8/1973 | Adams et al. | 260/515 A |
| 3,758,544 | 9/1973 | Alvarez | 260/465 F |
| 3,787,580 | 1/1974 | Fried et al. | 424/308 |
| 3,821,253 | 6/1974 | Fried et al. | 260/340.9 |
| 3,828,033 | 8/1974 | Nelson | 260/240 R |
| 3,873,594 | 3/1975 | Alvarez | 260/465 F |
| 3,896,157 | 7/1975 | Fried et al. | 260/469 |
| 3,904,682 | 9/1975 | Fried et al. | 260/520 |
| 3,904,683 | 9/1975 | Day et al. | 260/520 |
| 3,906,038 | 9/1975 | Fried et al. | 260/507 R |
| 3,914,293 | 10/1975 | Fried et al. | 260/512 C |
| 3,923,900 | 12/1975 | Petracek | 260/590 |
| 3,935,273 | 1/1976 | Fried et al. | 260/600 R |
| 3,958,012 | 5/1976 | Fried et al. | 424/333 |
| 3,959,364 | 5/1976 | Armitage et al. | 260/515 R |
| 3,960,936 | 6/1976 | Fried et al. | 260/488 CD |
| 3,960,957 | 6/1976 | Alvarez | 260/566 A |
| 3,975,432 | 8/1976 | Alvarez | 260/520 |
| 3,978,116 | 8/1976 | Fried et al. | 260/500.5 H |
| 3,978,124 | 8/1976 | Fried et al. | 260/558 R |
| 3,980,699 | 9/1976 | Fried et al. | 260/515 R |

(List continued on next page.)

FOREIGN PATENT DOCUMENTS

| | | |
|---|---|---|
| 59-10545 | 1/1984 | Japan . |
| 380563 | 9/1932 | United Kingdom . |

OTHER PUBLICATIONS

Horeau, et al; No. 287. "Steroids devoid of C nucleus (III). On a lactone corresponding to an isomer of bis-dehydroestrolactone"; Soc. Chim., 5th Series, '59 –Reports, pp. 1854–1857.

Marques, et al; "Facile Hydrodehalogenation with Hydrogen and Pd/C Catalyst under Multiphase Conditions"; J. Org. Chem. '93, vol. 58, No. 19, pp. 5266–5260.

DeVries et al; "Synthesis of High–Purity o–and p–Vinyltolouenes by the Heck Palladium–Catalyzed Arylation Reaction"; Organometallics (1994) vol. 13, pp. 2405–2411.

Heck; "Palladium Reagent sin Organic Syntheses"; Academic Press (1985), pp. 276–291.

Pinder; "The Hydrogenolysis of Organic Halides"; Synthesis, (1980), pp. 425–452.

Lewis; "Methylation of Phenol by Dimethyl Sulfate"; Industrial and Engineering Chemistry (1930), vol. 22, pp. 397–398.

(List continued on next page.)

Primary Examiner—Samuel Barts
Attorney, Agent, or Firm—E. E. Spielman, Jr.

[57] ABSTRACT

In producing (±)-2-(6-methoxy-2-naphthyl)propionic acid or precursor thereof from 2-bromo-6-methoxynaphthalene, use is made of 2-bromo-6-methoxynaphthalene formed by (a) methylating 6-bromo-2-naphthol with methyl chloride in a solvent comprising one or more compounds, RZ, where R is a hydrogen atom or an alkyl group, and Z is —OH or —CN provided that if Z is —CN, R is alkyl, and in the presence of a strong base; and (b) recovering and purifying 2-bromo-6-methoxynaphthalene so formed. Preferably, the 6-bromo-2-naphthol is formed by (1) reacting 1,6-dibromo-2-naphthol with hydrogen, in a solvent comprising (a) organic halide in which the halogen has an atomic number of 35 or less or (b) a mixture of water and such organic halide, and in the presence of catalytically effective amounts of (i) a tungsten carbide-based catalyst, and (ii) phase transfer catalyst; and (2) separating 6-bromo-2-naphthol from the organic halide solvent so that the 6-bromo-2-naphthol is substantially free of halogen-containing impurities before use in the above methylation reaction. This technology makes possible reductions in quantities of co-products formed, eliminates need for use of excess iron and/or dimethyl sulfate as reaction components, and makes possible improvements in plant operating efficiency. Precursors of (±)-2-(6-methoxy-2-naphthyl)propionic acid formed from such 2-bromo-6-methoxynaphthalene are Grignard reagent of 2-bromo-6-methoxynaphthalene, bis(6-methoxy-2-naphthyl)zinc, 6-methoxy-2-naphthylzinc halide, 6-methoxy-2-naphthyllithium, 6-methoxy-2-naphthylcopper(I), bis(6-methoxy-2-naphthyl)cadmium, 6-methoxy-2-naphthylcadmium halide, and 6-methoxy-2-vinylnaphthalene.

90 Claims, No Drawings

U.S. PATENT DOCUMENTS

| | | | |
|---|---|---|---|
| 3,988,365 | 10/1976 | Gallegra | 260/520 D |
| 3,994,968 | 11/1976 | Alvarez | 260/520 D |
| 3,998,966 | 12/1976 | Fried et al. | 424/308 |
| 4,001,301 | 1/1977 | Fried et al. | 260/473 F |
| 4,005,093 | 1/1977 | Zenitz | 260/293.62 |
| 4,009,197 | 2/1977 | Fried et al. | 260/473 F |
| 4,028,366 | 6/1977 | Zenitz | 260/293.62 |
| 4,045,485 | 8/1977 | Fried et al. | 260/566 A |
| 4,107,439 | 8/1978 | Walker et al. | 560/55 |
| 4,135,051 | 1/1979 | Walker | 560/105 |
| 4,142,054 | 2/1979 | Amin et al. | 560/105 |
| 4,144,397 | 3/1979 | Matthews et al. | 562/466 |
| 4,233,316 | 11/1980 | Gardocki | 424/317 |
| 4,239,914 | 12/1980 | Campolmi et al. | 562/466 |
| 4,246,164 | 1/1981 | Felder et al. | 260/501.17 |
| 4,246,193 | 1/1981 | Holton | 260/501.17 |
| 4,379,148 | 4/1983 | Sato et al. | 424/232 |
| 4,395,571 | 7/1983 | Dvorak | 562/466 |
| 4,545,992 | 10/1985 | Kamishita | 514/161 |
| 4,560,777 | 12/1985 | Giordano et al. | 549/374 |
| 4,571,333 | 2/1986 | Hsiao et al. | 424/22 |
| 4,605,758 | 8/1986 | Schloemer | 562/418 |
| 4,609,766 | 9/1986 | Giordano et al. | 568/592 |
| 4,621,152 | 11/1986 | Bernini | 562/401 |
| 4,623,736 | 11/1986 | Walker et al. | 549/369 |
| 4,628,123 | 12/1986 | Borsotti | 568/634 |
| 4,654,438 | 3/1987 | Schloemer | 562/496 |
| 4,665,224 | 5/1987 | Corvi Mora | 560/56 |
| 4,697,036 | 9/1987 | Giordano et al. | 562/418 |
| 4,723,033 | 2/1988 | Erickson | 560/56 |
| 4,734,507 | 3/1988 | Giordano et al. | 549/450 |
| 4,736,061 | 4/1988 | Piccolo et al. | 562/466 |
| 4,749,804 | 6/1988 | Schloemer | 558/51 |
| 4,766,225 | 8/1988 | Sayo et al. | 556/16 |
| 4,803,079 | 2/1989 | Hsiao et al. | 424/468 |
| 4,810,819 | 3/1989 | Giordano et al. | 562/56 |
| 4,857,462 | 8/1989 | Maier et al. | 435/197 |
| 4,864,063 | 9/1989 | Piccolo et al. | 568/328 |
| 4,919,803 | 4/1990 | Doyle et al. | 210/198.2 |
| 4,962,230 | 10/1990 | Takaya et al. | 562/433 |
| 5,034,416 | 7/1991 | Smith | 514/568 |
| 5,136,069 | 8/1992 | DeVries et al. | 556/453 |
| 5,243,068 | 9/1993 | DeVries et al. | 560/205 |
| 5,243,088 | 9/1993 | Jacquot et al. | 568/656 |
| 5,256,829 | 10/1993 | Jacquot | 568/737 |
| 5,315,026 | 5/1994 | Wu | 560/105 |
| 5,426,243 | 6/1995 | Lecouve | 568/737 |
| 5,536,870 | 7/1996 | Wu | 560/56 |

OTHER PUBLICATIONS

Ohta et al; "Asymmetric Hydrogenation of Unsaturated Carboxylic Acids Catalyzed by BINAP–Ruthenium(II) Complexes"; J. Org. Chem. (1987), vol. 52, pp. 3174–3176.

Rajagopal et al; "Mechanism of Palladium–Catalyzed Transfer Hydrogenolysis of Aryl Chlorides by Formate Salts[1]"; J. Org. Chem. (1995), vol. 60, pp. 1347–1355.

Alper et al; "The Regiospecific Palladium Catalysed Hydrocarboxylation of Alkenes under Mild Conditions"; J. Chem. Sol. Chem. Commun. (1983), pp. 1270–1271.

Horeau et al; "Steroides depourvus de noyau C (III). Sur une lactone correspondant a un isomere de la bis–dehydrocestrolacetone"; Memoires Presents A La Societe Chimique (1959), pp. 1854–1857.

Heitz et al; "Synthesis of monomers and polymers by the Heck reaction"; Makromoi Chem. (1988) vol. 189, pp. 119–127.

Marques et al; "Facile Hydrodehalogenation with $H_2$ and Pd/C Catalyst under Multiphase Conditions. 2. Selectivity and Kinetics"; J. Org. Chem. (1994) vol. 59, pp. 3830–3837.

Marques et al; "Facile Hydrodehalogenation with $H_2$ and Pd/C Catalyst under Multiphase Conditions. 3. Selective Removal of Halogen from Functionalized Aryl Ketones. 4. Aryl Halide–Promoted Reduction of Benzyl Alcohols to Alkanes"; J. Org. Chem. (1995), vol. 60, pp. 2430–2435.

Piccolo et al; "Zinc Salt Catalyzed Rearrangement of Acetals of Optically Active Aryl 1–Chloroethyl Ketones: Synthesis of Optically Active 2–Arylpropionic Acids and Esters[1]"; J. Org. Chem. (1987), vol. 52, pp. 10–14.

Stinson; "Technological Innovation Thrives in Fine Chemicals Industry"; Science/Technology; (1996), pp. 35–61.

PRODUCTION OF RACEMIC 2-(6-METHOXY-2-NAPHTHYL) PROPIONIC ACID OF PRECURSORS THEREOF

TECHNICAL FIELD

This invention relates to processes for the synthesis of (±)-2-(6-methoxy-2-naphthyl)propionic acid or precursors thereof, and more particularly to novel environmentally-friendly process technology suitable for producing such materials on a commercial scale.

BACKGROUND

Naproxen, d-2-(6-methoxy-2-naphthyl)propionic acid, and its sodium salt are well known non-steroidal antiinflammatory agents described for example in U.S. Pat. Nos. 3,904,682; 3,998,966; and 4,009,197. While various synthesis procedures for its production have been proposed and studied, highly efficient procedures utilize 2-bromo-6-methoxynaphthalene (also known as 6-bromo-2-methoxynaphthalene) as a key starting material or chemical intermediate. This material product is usually formed by hydrodebromination of 1,6-dibromo-2-naphthol by use of iron powder in an aqueous acid medium to form 6-bromo-2-naphthol, followed by treatment with dimethyl sulfate and sodium hydroxide to effect methylation of the hydroxyl group. Unfortunately this process approach suffers from need for long cycle times, formation of large amounts of co-products from both reaction steps, need for use of stoichiometric excesses of dimethyl sulfate and iron, and lower than desired plant throughput. Another method of producing 2-bromo-6-methoxynaphthalene is suggested in U.S. Pat. No. 5,256,829 where hydrodebromination of 1,6-dibromo-2-naphthol to 6-bromo-2-naphthol is effected by use of hydrogen and a tungsten carbide-based catalyst in an acidic organic solvent, and where the reagents taught for use in the methylation step are methyl sulfate or methanol. Despite the intensity and scope of prior investigations of such process steps, a need exists for process technology capable of reducing the quantities of by-product wastes formed in the operation, of avoiding the need for use of excess iron and/or dimethyl sulfate as reaction components, and of improving the overall efficiency of plant operation when conducted on a large scale.

This invention is deemed to fulfill this need in an efficient and effective manner.

SUMMARY OF THE INVENTION

In one of its embodiments this invention provides improvements in a process for production of (±)-2-(6-methoxy-2-naphthyl)propionic acid or precursor thereof from 2-bromo-6-methoxynaphthalene. The improvements involve using in the process a 2-bromo-6-methoxynaphthalene product formed by a process comprising:

a) methylating 6-bromo-2-naphthol with methyl bromide or, preferably, methyl chloride in a halogen-free liquid solvent comprising at least 40% by weight of one or more compounds of the formula RZ where R is a hydrogen atom or an alkyl group, and Z is a hydroxyl group or a cyanide group with the proviso that if Z is a cyanide group, R is an alkyl group, and in the presence of at least one strong base such that 2-bromo-6-methoxynaphthalene is formed.

The so formed 2-bromo-6-methoxynaphthalene precursor is preferably recovered and purified for further reaction to obtain the (±)-2-(6-methoxy-2-naphthyl)propionic product.

Another embodiment is the use, in a process for the production of (±)-2-(6-methoxy-2-naphthyl)propionic acid or precursor thereof, of 2-bromo-6-methoxynaphthalene formed by a process which comprises:

A) reacting 1,6-dibromo-2-naphthol with hydrogen or a precursor compound that generates nascent hydrogen in the medium of the reaction, in a halogen-containing liquid solvent comprising at least about 50% by weight of (a) at least one liquid organic halide solvent in which the halogen content has an atomic number of 35 or less or (b) a mixture of water and at least one such liquid organic halide solvent, and in the presence of catalytically effective amounts of (i) a tungsten carbide-based catalyst, and (ii) at least one phase transfer catalyst, such that 6-bromo-2-naphthol is formed;

B) separating 6-bromo-2-naphthol so formed from said organic halide solvent so that the 6-bromo-2-naphthol is at least substantially completely free from any halogen-containing impurity content;

C) methylating 6-bromo-2-naphthol from B) with methyl bromide or methyl chloride, or both, in a halogen-free liquid solvent comprising at least about 40% by weight of one or more compounds of the formula RZ where R is a hydrogen atom or an alkyl group, and Z is a hydroxyl group or a cyanide group with the proviso that if Z is a cyanide group, R is an alkyl group, and in the presence of at least one strong base such that 2-bromo-6-methoxynaphthalene is formed; and D) preferably, recovering and purifying 2-bromo-6-methoxynaphthalene so formed.

Other embodiments of this invention make it possible not only to produce (±)-2-(6-methoxy-2-naphthyl)propionic acid and/or one or more precursors of (±)-2-(6-methoxy-2-naphthyl)propionic acid such as, for example, Grignard reagent of 2-bromo-6-methoxynaphthalene (variously described as 6-methoxy-2-naphthylmagnesium bromide and 2-(6-methoxynaphthyl)magnesium bromide, bis(6-methoxy-2-naphthyl)zinc, 6-methoxy-2-naphthylzinc halide (chloride, bromide, iodide), 6-methoxy-2-naphthyllithium, 6-methoxy-2-naphthylcopper(I), bis(6-methoxy-2-naphthyl)cadmium, 6-methoxy-2-naphthylcadmium halide (chloride, bromide, iodide), 6-methoxy-2-vinylnaphthalene, etc., but also to produce 6-bromo-2-naphthol and 2-bromo-6-methoxynaphthalene on a large scale by highly efficient, environmentally-friendly processes. Indeed, the process technology of this invention is capable of producing these materials of a purity suitable for use in the production of nabumetone, another well-known non steroidal antiinflammatory agent, as well as for use in (±)-2-(6-methoxy-2-naphthyl)propionic acid synthesis.

These and other embodiments and features of this invention will be still further apparent from the ensuing description and appended claims.

FURTHER DESCRIPTION OF THE INVENTION

Methylation of 6-Bromo-2-Naphthol

As noted above, this invention involves, inter alia, the process of methylating 6-bromo-2-naphthol with methyl bromide or, preferably, methyl chloride to produce 2-bromo-6-methoxynaphthalene. Use of these methylating reagents, especially methyl chloride, instead of dimethyl sulfate is of considerable advantage in that large excesses of dimethyl sulfate (60–70%) are normally required for adequate yields of the desired product. Furthermore, the reaction with dimethyl sulfate utilizes only one of the two methyl groups and consequently leads to the generation of an aqueous co-product stream containing sodium methyl sulfate. The safe and environmentally satisfactory disposal of such a stream is not without considerable difficulty and expense.

Pursuant to this invention, the methylation with methyl bromide or methyl chloride is performed in a halogen-free liquid solvent comprising at least 40% by weight (preferably in the range of about 40 to about 70% by weight) of one or more compounds of the formula RZ where R is a hydrogen atom or an alkyl group, and Z is a hydroxyl group or a cyanide group (with the proviso that if Z is a cyanide group, R is an alkyl group), and in the presence of at least one strong base. These solvents thus include water, alcohols, nitriles, and mixtures thereof. Of these materials water, one or more alcohols, and mixtures, especially single phase mixtures of water and one or more alcohols are preferred from the cost effectiveness standpoint. Suitable nitriles include acetonitrile, propionitrile, butyronitrile, α-methylbutyronitrile, benzonitrile, and similar liquid cyclic and acyclic nitriles, including mixtures of two or more such materials. Aliphatic and alicyclic alcohols, including diols, suitable for use include methanol, ethanol, 1-propanol, 2-propanol, 1-butanol, 2-methyl-1-propanol, 1-pentanol, 1-hexanol, cyclopentanol, 2-ethoxyethanol, ethylene glycol, and analogous compounds, including mixtures of two or more such alcohols. Of these solvents, liquid lower alkanols having 2 to 4 carbon atoms, especially 2-propanol, and single phase mixtures of lower alkanols with water, especially mixtures of 2-propanol and water, are preferred. More preferred are solvents composed of at least 98 weight percent or more of a liquid alcohol, of which substantially pure 2-propanol, or substantially pure 2-propanol containing up to about 2 wt % water, are especially preferred.

It is of great importance to ensure that the reaction mixture used in the methylation process is free of organic halogen-containing impurities as such materials, if present, can react with the 6-bromo-2-naphthol and/or 2-bromo-6-methoxynaphthalene to produce undesirable by-products.

The methylation reaction is performed in the presence of a strong base, i.e., in a strongly basic liquid reaction medium. For this purpose the most cost effective bases comprise inorganic bases such as the oxides and hydroxides of sodium and potassium. Use of such materials with water or suitable alcohols or combinations of one or more suitable alcohols with water serve as examples of such media. Suitable organic bases that can be used include sodium or potassium alkoxides (e.g., sodium methoxide, potassium methoxide, sodium ethoxide, potassium ethoxide, sodium isopropoxide, potassium isopropoxide, etc.), alkaline amide salts (e.g., sodium amide, potassium amide, sodium isopropyl amide, potassium ethylamide, etc.), and similar materials. As is well known to chemists, upon addition to water or alcohols certain bases such as the hydroxides lose their identity while in solution by virtue of ionization. Likewise the oxides undergo transformations so that ionization occurs and upon drying of the solution the hydroxide remains. As will be made even clearer hereinafter, this invention is not limited in any way by preliminary changes or transformations which occur as a natural consequence of bringing two or more materials together. For example, addition of sodium hydroxide to an alcohol such as 1-propanol is generally regarded as resulting in the formation of an alkoxide, in this case, sodium propoxide. But for the purposes of this invention the actual composition of the material while in solution is immaterial.

The methylation process of this invention is usually performed at temperatures in the range of about 25° and about 140° C., and preferably in the range of about 50° and about 100° C. The mole ratio of methyl bromide or methyl chloride to 6-bromo-2-naphthol will usually be in the range of about 1.0 to about 1.2 moles of the methyl halide per mole of the 6-bromo-2-naphthol. The reaction solution will generally contain from about 1.0 to about 1.1 mole percent of added strong base per mole of 6-bromo-2-naphthol charged. Reaction periods in the range of about 1 hour to about 6 hours will usually suffice. The reaction is conveniently conducted in a closed reaction vessel under autogenous pressure, but can be performed under various pressure conditions ranging from atmospheric pressures to superatmospheric pressures (e.g., 100–200 psig).

To date, experience has shown that the use of methyl chloride is much preferred over use of methyl bromide as the latter, while operable, has yielded products containing one or two major impurities in the range of about 10–15 wt %. Based on these results, methyl iodide should also be an operable methylating agent for use in the process, and is expected to lead to the desired product in high yields.

The following examples illustrate preferred procedures for conducting the methylation reaction in accordance with this invention. In the examples the following abbreviations are used: 6-BN is 6-bromo-2-naphthol; BMN is 2-bromo-6-methoxynaphthalene; MBMN is 2-bromo-6-methoxy-ar-methylnaphthalene, a by-product impurity; DBMN is dibromomethoxynaphthalene, an impurity; TBMN is tribromo-methoxynaphthalene, another impurity; MN is methoxynaphthalene; 1,6-DBN is 1,6-dibromo-2-naphthol, TBAB is tetrabutylammonium bromide; and EDC is ethylene dichloride.

EXAMPLE 1

Methylation with Methyl Chloride in Water

A 300 mL autoclave was charged with 6-BN (0.2 mol, 44.6 g), sodium hydroxide (0.25 mol, 20g of 50%), water (140 mL) and then purged with nitrogen and sealed. Methyl chloride (0.3 mol, 15.8 g) was added and the reaction mixture was heated at 125° C. for five hours. The pressure reached a maximum of 150 psig. At the end, the reactor was cooled to room temperature and excess methyl chloride was released into scrubbers. Solid BMN was filtered from the acidic aqueous phase. Analysis of the solid showed 87% BMN, 8% unreacted 6-BN, 4% MBMN, and 1% methoxynaphthalene.

EXAMPLE 2

Methylation with Methyl Chloride in Isopropyl Alcohol

Sodium hydroxide (0.22 mol, 8.8 g; 17.6 g of 50%) was added to isopropyl alcohol (120 g; 150 mL). The stirred mixture was degassed with nitrogen and then 6-BN (0.2 mol, 44.6 g) was added. The resulting solution was purged with nitrogen and placed in an autoclave and charged with methyl chloride (0.47 mol, 24 g) which dissolved in the solution very rapidly at room temperature. The mixture was heated to 66° C. and achieved a maximum pressure of 80 psig. The pressure stabilized after about four hours. The mixture was then heated at 80° C. for another two hours and then cooled. Excess methyl chloride was released into traps and the autoclave was opened. The yellow solid mass was filtered and washed with water. GC analysis of the crude showed only BMN. The product was dried under vacuum (42.6 g, 90%) and analyzed by GC and GC-mass spec.: 99.4 wt % BMN, 0.06% MN, 0.04% 6-BN, 0.2% DBMN.

EXAMPLE 3

Hydrodebromination of 1,6-Dibromo-2-Naphthol

A solution of 1,6-dibromo-2-naphthol (DBN) (196 g, 0.65 mol) in EDC (348 g) is charged in a one-liter Hastalloy B autoclave. Tungsten carbide (43.7 g, 20 wt %) and tetrabutylammonium bromide (1.1 g, 0.5 wt %) are added and the reactor is sealed. The reactor is purged with hydrogen (50 psig) and vented three times and then pressured with hydrogen and heated to 110C. A constant purge of hydrogen is maintained at such a rate that the pressure remains in the 100–110 psig range. Analysis of a product mixture formed in this general manner showed 92.3% 6-BN, 0.8% DBN, and 1.9% 2-naphthol. The reactor is cooled to room temperature, vented to scrubbers, and the WC catalyst is permitted to settle. The EDC solution is removed through the dip tube. A portion of the EDC solution is concentrated by distillation. When the pot temperature reaches around 100° C., water (50 mL) is added to azeotropically remove the remainder of EDC without raising the temperature of the crude 6-BN. When all of the EDC is removed (judged by the overhead temperature) the crude is analyzed. In an operation conducted in this general manner the crude product was found to contain 6-BN (55 g, 250 mmol) as the major component.

Methylation of 6-BN with Methyl Chloride

Isopropyl alcohol (150 mL) and sodium hydroxide (11 g, 280 mmol; 22 g of 50% solution) were added to such crude product and the mixture was sealed in an autoclave. Methyl chloride (18 g, 350 mmol) was introduced at room temperature and the autoclave was heated to 76° C. After four hours the reaction was stopped and the excess methyl chloride was removed. A solid mass was recovered with little liquid phase. The slurry had a pH of 12–13, and was acidified by dilute hydrochloric acid. Isopropyl alcohol was removed by simple distillation and water (100 mL) was added to the residue. The mixture was heated to about 100° C. (which melted the crude) with fast stirring. The mixture was settled and the aqueous layer was separated from the molten BMN. BMN was distilled under reduced pressure (1 mm Hg, 160°–165° C.). The white solid distillate was crystallized from isopropyl alcohol (200 mL). The white solid (42 g, 72%) was analyzed by GC: BMN 97.1 wt %, MBMN 0.2%, MN 0.1%, DBMN 0.6%, and TBMN 2.0%.

EXAMPLE 4

Methylation with Methyl Chloride in Acetonitrile

To a solution of 6-BN (15.6 g, 70 mmol) in acetonitrile (50 mL) was added potassium hydroxide pellets (4.5 g, 80 mmol) and tetrabutylammonium bromide (0.5 g). The resulting mixture was transferred to an autoclave and charged with methyl chloride (6 g, 120 mmol) and heated to 70° C. After three hours it was cooled to room temperature. Analysis of the crude reaction mixture showed only BMN.

EXAMPLE 5

Methylation with Methyl Chloride in Acetonitrile

The above reaction was repeated with 6-BN from a regioselective hydrodebromination reaction conducted as described in detail hereinafter, and with sodium hydroxide pellets. The crude product contained: 98.4% BMN, 1.0% 6-BN, 0.4% DBMN, 0.1% MN.

EXAMPLE 6

Methylation with Methyl Chloride in Acetonitrile

The above reaction was repeated with 50% sodium hydroxide and 6-BN, formed by a regioselective hydrodebromination reaction. Analysis of the crude showed: 96.8% BMN, 0.4% MN, 1.4% 6-BN, 0.6% DBMN, others 0.8%.

EXAMPLE 7

Bromination of 2-Naphthol

2-Naphthol (144.8 g, 1.00 mol), EDC (537 g), and water (162 g) were charged to a 2-L reactor equipped with a reflux condenser, mechanical stirrer and peristaltic pump addition system. The reactor was heated to about 55° C. until most of the β-naphthol was dissolved. Bromine (336.9 g, 2.11 mol) was then added (sub-surface) via the pump at such a rate so as to maintain the reaction temperature at 60° C. After the bromine addition, the reaction temperature was maintained at 60° C. for 1.5 h. The reaction was then cooled slightly and the lower phase (aq. HBr) siphoned off. The remaining EDC solution (841 g) was transferred out of the reactor and analyzed by GC which showed 0.4% 2-naphthol, 92.6% 1,6-dibromo-2-naphthol (1,6-DBN), and 4.9% of other isomers.

Hydrodebromination of 1,6-Dibromo-2-Naphthol

A solution of 1,6-DBN (271 g, 0.9 mol) in EDC (551 g), obtained from the bromination reaction, was charged in a 1000 mL Hastalloy B autoclave. Tungsten carbide (82 g, 30 wt %) and tetrabutylammonium bromide (0.2 g, 0.1 wt %) were added and the reactor was sealed. The reactor was purged with hydrogen (50 psig) and vented three times and then pressured with hydrogen and heated to 90° C. A constant purge of hydrogen was maintained in such a rate that the pressure remained in the 120–125 psig range. Analysis of the reaction mixture after 5.5 hours showed 90% 6-BN, 2% DBN, and 2% 2-naphthol. The reactor was cooled to room temperature, vented to scrubbers, and the catalyst was permitted to settle. The EDC solution (747 g) was removed through the dip tube.

Methylation of 6-BN with MeCl

The EDC solution was transferred to a 1,4-liter (three pints) Chemco glass reactor with stainless steel head. It was first neutralized with dilute acid and then concentrated by distillation. Water (50 mL) was added to azeotropically remove traces of EDC left in the residue. Isopropyl alcohol (242 g) and sodium hydroxide (44 g, 1.1 mol; 88 g of 50% solution) were charged into the reactor. The reactor was sealed, purged with nitrogen, and heated to 70° C. Methyl chloride (66 g, 1.3 mol) was charged over a period of one hour (40–50 psig). After stirring at 80° C. for another hour, isopropyl alcohol was removed by distillation. The residue was heated to melted condition (90°–95° C.) and then it was washed with water (400 g). Water was removed and the residue was distilled under vacuum (1 mmhg). After removing small amounts of volatile materials, BMN was distilled at 160°–165° C. as a white solid (169 g). Isopropyl alcohol (490 g) was added and the solution was heated to reflux and then slowly cooled down to about 10° C. Solid BMN was removed and washed with cold (0° C.) isopropyl alcohol (180 g) and then dried under vacuum at 70°–75° C. Analysis of the white crystalline product showed 99.7 wt % BMN.

As illustrated in Example 7, upon completion of the methylation reaction, the 2-bromo-6-methoxynaphthalene is recovered and purified. While several different procedures may be envisioned and utilized for accomplishing this, it is important to ensure that the product is of sufficient purity to meet the stringent requirements for use in the synthesis of (±)-2-(6-methoxy-2-naphthyl)propionic acid. In accordance with preferred embodiments of this invention two different, but related, procedures have been developed for accomplishing the recovery and purification of 2-bromo-6-methoxynaphthalene when the base used in the methylation reaction is an alkali metal base such as sodium hydroxide or potassium hydroxide. In one such embodiment, the separation and recovery is effected by a procedure which comprises in essence the following three-steps:

1) distilling off the solvent from the methylation reaction product mixture to leave a hot molten residue;
2) washing the residue, while molten, with water to remove alkali metal halide by-product and water-soluble impurities, if any, from the 2-bromo-6-methoxynaphthalene-containing residue; and
3) crystallizing the 2-bromo-6-methoxynaphthalene from a suitable liquid medium.

As the crystallization medium for this procedure, use can be made of liquid alcohols, ethers, ketones, nitrites, hydrocarbons, halogenated hydrocarbons, carboxylic acids, and the like. Of such materials, liquid lower alkanols ($C_{1-4}$), especially 2-propanol, are preferred. Mixed solvent systems can also be used, if desired.

The other procedure of this invention for recovering and purifying the 2-bromo-6-methoxynaphthalene comprises in essence four steps, as follows:

1) distilling off solvent from the methylation reaction product mixture to leave a hot molten residue;
2) washing the residue, while molten, with water to remove alkali metal halide by-product and water-soluble impurities, if any, from the residue;
3) distilling 2-bromo-6-methoxynaphthalene from the washed residue; and
4) crystallizing the 2-bromo-6-methoxynaphthalene from a liquid medium.

Here again, the liquid lower alkanols, especially 2-propanol, are preferred for use as the crystallization medium of this procedure. However, as above, use can also be made of liquid ethers, ketones, nitrites, hydrocarbons, halogenated hydrocarbons, carboxylic acids, and the like, including mixed solvent systems.

Production of 6-Bromo-2-Naphthol

Another embodiment of this invention is an efficacious process for the production of 6-bromo-2-naphthol of a purity and composition such that it is eminently suited and especially adapted for use in the above methylation process of this invention. More particularly, this process comprises reacting 1,6-dibromo-2-naphthol with hydrogen or a precursor compound that generates nascent hydrogen in the medium of the reaction. This reaction is performed in a halogen-containing liquid solvent comprising at least 50% by weight of (a) at least one organic halide solvent or (b) a mixture of water and at least one organic halide solvent, such as, for example, a polychloroalkane. In addition, the reaction is performed in the presence of catalytically effective amounts of (i) a tungsten carbide-based catalyst, and (ii) at least one phase transfer catalyst. The 6-bromo-2-naphthol formed in the reaction is separated from (and freed of) the organic halide solvent so that the 6-bromo-2-naphthol is at least substantially completely free from any halogen-containing impurity content. It will be noted that this is a controlled or selective hydrodebromination reaction wherein one of two bromine atoms of the reactant is removed in preference to the other, and the one that remains is in the desired position. Thus, the reaction is in fact a regiospecific or regioselective hydrodebromination reaction. These and terms of similar import may be employed hereinafter to refer to this particular reaction.

The liquid organic halides used as solvent media for the hydrodebromination reaction are liquids composed of carbon and halogen atoms, and in most cases hydrogen atoms as well. The halogen content of such solvents is one or more fluorine, chlorine and/or bromine atoms (i.e., halogen of atomic number 35 or less). Thus, the solvent medium for the hydrodebromination reaction can be one or more perhalocarbons or one or more halohydrocarbons or a mixture of one or more perhalocarbons or one or more halohydrocarbons, in all cases where the halogen atom content has an atomic number of 35 or less. These solvents can have one or more halogen atoms in the molecule, and when two or more halogen atoms are present in the molecule, they can be the same or different halogen atoms (i.e., they can be fluorine and chlorine atoms, chlorine and bromine atoms, fluorine and bromine atoms, or fluorine, chlorine and bromine atoms). Preferred solvents for this reaction are the halogen-containing saturated aliphatic compounds, halogen-containing saturated cycloaliphatic compounds and halogen-containing aromatic compounds, and of these the chloroalkanes are preferred. Most preferred are polychloroalkanes, especially ethylene dichloride. These solvents may be used in combination with water as a mixed phase reaction medium. Preferably, however, the halocarbon or halohydrocarbon solvent is either anhydrous or it contains small amounts of water and in this latter case, the amount of water is preferably small enough such that the solvent remains visually clear and thus does not possess a visually readily-observable separate liquid phase. The foregoing solvents are desirable media in which to perform this regiospecific or regioselective hydrodebromination reaction. Likewise, the conjoint use of tungsten carbide and phase transfer catalyst in conjunction with such reaction media have afforded both high selectivity and shortened reaction periods. It will be recalled, however, that if the 6-bromo-2-naphthol used in the methylation process is contaminated with organic halogen-containing impurities, the resultant methylation product will, in all likelihood, suffer from the presence of one or more by-products from the interaction of the organic halogen-containing impurities with the 6-bromo-2-naphthol and/or the 2-bromo-6-methoxynaphthalene under the conditions of the methylation reaction. Thus, another feature of this process for producing 6-bromo-2-naphthol is the preferred methods by which the 6-bromo-2-naphthol formed in the reaction is separated from (and freed of) the halocarbon and/or halohydrocarbon utilized as the reaction medium or together with water in the reaction medium.

A few examples of halocarbons and halohydrocarbons that can serve as a reaction medium for the regiospecific hydrodebromination reaction include hexafluorobenzene, octafluorotoluene, perfluorodecalin, carbon tetrachloride, chloroform, ethylene dibromide, 1,1-dibromoethane, bromobenzene, chlorobenzene, fluorobenzene, 1-bromo-3-chlorobenzene, 1-chloro-4-fluorobenzene, o-bromotoluene, m-bromotoluene, o-chlorotoluene, m-chlorotoluene, p-chlorotoluene, o-fluorotoluene, m-fluorotoluene, p-fluorotoluene, α-chloro-α,α-difluorotoluene, 1,1,1,2-tetrachloro-2,2-difluoroethane, 1,1,2,2-tetrachloro-1,2-difluoroethane, 1,1,2-tribromoethane, bromocyclohexane, chlorocyclohexane, trichloroethylene, perchloroethylene, and like compounds.

Polychloroalkanes suitable for use as reaction media for the conversion of 1,6-dibromo-2-naphthol to 6-dibromo-2-naphthol include ethylene dichloride (1,2-dichloroethane), 1,1-dichloropropane, 1,2-dichloropropane, 1,3-dichloropropane, 1,1,1-trichloroethane, 1,1,2-trichloroethane, 1,1,2,2-tetrachloroethane, and dichloromethane. Of these, ethylene dichloride is most preferred.

When water is present in the organic halide solvent, it is desirable to avoid an amount of water that will deactivate the catalyst. Thus, the amount of water used is usually less than 10% by weight of the total weight of water plus halocarbon and/or halohydrocarbon solvent. A particularly preferred reaction medium is a visually clear mixture composed of ethylene dichloride and water in which the amount of water is below or up to, but not in excess of, the saturation point when the mixture is at 25° to 30° C. The reaction medium should be essentially free of iron or other dissolved metals that would interfere with the reaction.

The tungsten carbide catalysts used in this reaction are catalysts based on tungsten carbide. The use of such catalysts per se in the hydrodebromination of 1,6-dibromo-2-naphthol with hydrogen to form 6-dibromo-2-naphthol has been reported heretofore, in U.S. Pat. No. 5,256,829 to R. Jacquot. According to the patent, the tungsten carbide catalysts may also comprise, in addition to the tungsten carbide, one or more other metal monocarbides, for example the carbides of molybdenum, vanadium, niobium, tantalum, titanium, iron and chromium. When present, the amount of these other metal carbides is indicated to preferably be in the range of about 0.01% to about 50% by weight with respect to the total amount of all carbides present. According to the patent, the catalyst can be based either on use of bulk tungsten carbide, or on use of supported tungsten carbide, in either case with or without the co-presence of one or more carbides of other metals. Oxides, such as silica, alumina and titanium dioxide, or charcoal, are said to be useful as supports. The patent also refers to use of a monolithic substrate (honeycomb or otherwise) of tungsten carbide or of a monolithic substrate coated with a layer of tungsten carbide, and of finely divided product and made of, or coated with, tungsten carbide. Use of products made by shaping pulverulent materials (powders) such as beads, pellets, spheres, granules, extrudates, agglomerates and others, with a circular, oval, trilobate or multilobate, solid or hollow cross-section is also referred to in the patent. The patent further indicates that tungsten carbide can be used whose specific surface area (BET) ranges from 0.01 to several hundreds of m²/g and, in particular, from 1 to 300 or 400 m²/g.

Most preferably, the tungsten carbide catalyst used in the practice of this invention is in the form of essentially pure tungsten carbide itself in a very fine powdery state, e.g., with an average particle size of about 0.9 micron and containing particles as small as 0.1 micron. Such material has been found to be highly effective when utilized in accordance with the co-catalyzed selective hydrodebromination process of this invention.

Amounts of tungsten carbide-based catalyst are typically in the range of about 5 to about 50 wt % of WC based on the weight of 1,6-dibromo-2-naphthol initially present in the reaction mixture. Preferred amounts of the above preferred finely-divided tungsten carbide are in the range of about 10 to about 30 wt % of WC based on the weight of 1,6-dibromo-2-naphthol initially present.

In the regiospecific hydrodebromination process of this invention, a co-catalyst is employed, namely, at least one phase transfer catalyst. For this purpose use can be made of various types of phase transfer catalysts such as crown ethers, crypt compounds, quaternary phosphonium complexes, and quaternary ammonium complexes. Of these, the quaternary ammonium complexes are most preferred.

Suitable quaternary ammonium complexes include compounds depicted by the formula:

where $R^1$, $R^2$, $R^3$ and $R^4$ are, independently, hydrocarbyl groups (e.g., alkyl, cycloalkyl, aryl, aralkyl, alkenyl, alkoxylated alkylene polyamine groups, alkoxylated hydroxyhydrocarbyl groups, and/or heterocyclic groups in which the heteroatom or atoms are nitrogen atoms), and X is an anion such as a halide ion, a hydroxyl anion, a monoalkylsulfate anion, a sulfonate anion, a hydrogen sulfate anion, or the like. Examples of such compounds include:

tetrabutylammonium bromide
tetrahexylammonium bromide
trimethyldodecylammonium chloride;
trimethyldodecylammonium bromide;
trimethyltetradecylammonium chloride;
trimethyltetradecylammonium bromide;
trimethylhexadecylammonium chloride;
trimethylhexadecylammonium bromide;
trimethyloctadecylammonium chloride;
trimethyloctadecylammonium bromide;
dimethylalkylbenzylammonium chloride; where the alkyl groups are one or more of the following: n-$C_{12}H_{25}$; n-$C_{14}H_{29}$; n-$C_{16}H_{33}$; n-$C_{18}H_{37}$;
methylbis(2-hydroxyethyl)octadecylammonium chloride;
methylpolyoxyethylene (15) octadecylammonium chloride;
n-dodecyl (61%), n-tetradecyl (23%) dimethylbenzylammonium chloride;
n-tetradecyl (60%), n-hexadecyl (30%) dimethylbenzylammonium chloride;
n-dodecyl (40%), n-tetradecyl (50%) dimethylbenzylammonium chloride;
n-dodecyl (61%), n-tetradecyl (23%) dimethylbenzylammonium chloride;
n-octadecyldimethylbenzylammonium chloride;
42% solution of mixed n-tetradecyl (40%) and n-hexadecyl (60%) dimethylbenzylammonium chlorides;
8% solution of dialkylmethylbenzylammonium chloride;
n-dodecyl (35%), tetradecyl (5%), hexadecyl (60%) dimethylbenzylammonium chloride;
n-dodecyl (20%), tetradecyl (50%), hexadecyl (30%) dimethylbenzylammonium bromide;
methyl sulfate quaternary of ethoxylated tallow diethylenetriamine condensate;
methyl sulfate quaternary of propoxylated tallow diethylenetriamine condensate; and
1-(tallow amidoethylene)-2-nor(tallow alkyl)-2-imidazolinium, methyl sulfate quaternary.

Methods of preparation for the quaternary ammonium compounds useful in carrying out the process of this invention are numerous and vary depending on the structure of the final compound. Typical reactions are, for example, reaction of a suitable tertiary amine with an alkylating agent, which can be an alkyl ester or alkyl halide. Such reactions are summarized in Kirk-Othmer, *Encyclopedia of Chemical Technology*, Third Edition, Volume 19.

The quaternary ammonium complex is used in a co-catalytically effective amount, typically in the range of about 0.01 to about 10 wt %, and preferably in the range of about 0.1 to about 1 wt %, of the 1,6-dibromo-2-naphthol initially present.

Quaternary phosphonium complexes which may be employed include compounds depicted by the formula:

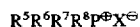

where $R^5$, $R^6$, $R^7$ and $R^8$ are, independently, substantially straight chain hydrocarbyl groups (e.g., alkyl, alkenyl, alkoxyalkyl, poly(alkoxy)alkyl, etc., groups which are either non-branched or if branched, have branching in remote positions that do not provide steric hindrance), and X is an anion such as a halide ion. Methods for the preparation of such complexes include reaction of phosphine with sterically unhindered alkyl halides. Examples of such compounds include: tetrabutylphosphonium bromide, hexadecytributylphosphonium chloride, methyltriphenylphosphonium iodide, 2-hydroxyethyltriphenylphosphonium bromide, tetrabutylphosphonium chloride, tetraphenylphosphonium chloride, tetraphenylphosphonium bromide, tetrabutylphosphonium iodide, methyltrioctylphosphonium bromide, and analogous compounds.

Co-catalytically effective amounts of quaternary phosphonium complex used will typically fall in the range of about 0.01 to about 10 wt %, and preferably in the range of about 0.1 to about 1 wt %, of the 1,6-dibromo-2-naphthol initially present.

For descriptions of crown ethers such as 18-crown-6 and crypt compounds such as crypt-222 which may be used in the process, one may refer, for example to such references as U.S. Pat. No. 3,687,978; J. J. Christensen, et al., *Chem. Rev.*, 1974, 74, 351; J. S. Bradshaw, et al., *Heterocycl. Chem.*, 1974, 11, 649; C. J. Pedersen, et al., *Angew. Chem. Int. Ed. Engl.*, 1972, 11, 16; the Technical Bulletin of PCR Incorporated entitled KRYPTOFIX; and *J. Org. Chem*, 1977, Vol 42, No. 10, 2A. The crown ether or crypt compound is used in a catalytically effective amount, which typically is in the range of about 0.01 to about 0.1 mole per mole of 1,6-dibromo-2-naphthol initially present in the reaction mixture.

To initiate the catalyzed regiospecific hydrodebromination reaction, the reaction system should contain a small catalytically effective amount of an acidic substance, most preferably hydrogen bromide. This is typically an amount within the range of about 1 to about 10 wt % of the total weight of the reaction system that ensures that the reaction is initiated and proceeds at a satisfactory rate without at the same resulting in the formation of appreciable quantities of 2-naphthol through overhydrodebromination. The optimum amount in any case should be determined by performing a few pilot tests, as the amount appears to depend upon a number of factors which can vary from case to case and which have defied repeated attempts of identification and quantification, such as the reaction and reaction conditions used to form the 1,6-dibromo-2-naphthol, the purity of the initial 1,6-dibromo-2-naphthol, the amount and makeup of the impurities in the initial 1,6-dibromo-2-naphthol, the materials of construction to which the 1,6-dibromo-2-naphthol was exposed during its formation and before its use, the duration of such exposure, and perhaps other factors.

Experimental studies conducted to date indicate that the tungsten carbide catalyst undergoes little if any change during the course of a number of successive runs. Nevertheless it is entirely possible that during the reaction the tungsten carbide catalyst may enter into transitory changes such as coordinating with or otherwise accepting hydrogen atoms on its surface, and/or forming some form of transitory complex with the phase transfer catalyst. In short, it is not known exactly how (i.e., the mechanism by which) either catalyst component actually functions during the reaction nor the actual state or composition of the catalyst components when functioning in the reaction mixture. Therefore, as regards catalyst composition, the co-catalyst materials are identified herein as to their respective compositions prior to being combined with any other substance being used in the process. After addition to, and/or mixing with, one or more other components used in the process and/or during the course of the process itself, either or both co-catalysts may change in its respective composition, and if so, the resultant changed material—whatever its makeup and however many changes it may undergo—may be in whole or in part responsible for the functioning of the catalyst.

As indicated above, it is highly desirable, if not highly important, to ensure that the liquid phase of the controlled hydrodebromination reaction contains an acidic catalyst most preferably hydrogen bromide during at least substantially the entire reaction period of such hydrodebromination reaction. Accordingly, unless absolutely pure 1,6-dibromo-2-naphthol is available for use as the starting material (in which case a small catalytically effective amount of an acidic catalyst, most preferably hydrogen bromide, is introduced into the reaction mixture), a small amount of hydrogen bromide should be added to ensure initiation of the reaction. From then on it is particularly preferred, and important when seeking the best results achievable from the practice of this invention, to control the amount of hydrogen bromide by-product remaining in the liquid phase by purging the reaction mixture with hydrogen or an inert gas such as nitrogen, argon, neon, etc., so that most of the by-product hydrogen bromide is continuously removed as it is formed while still leaving a small catalytically effective amount of hydrogen bromide dissolved in the liquid reaction medium. The rate of purging is best determined in any given situation by running a few pilot experiments and determining by analysis of the product, the amount of "overhydrodebrominated" product that exists in the product. If too much hydrogen bromide is left in the product, the amount of non-brominated 2-naphthol will become excessive. Conversely, if too little hydrogen bromide is left in the liquid phase, incomplete reactions with excessive amounts of brominated products will result. Thus, the rate of purge is controlled such that the recovered 6-bromo-2-naphthol product on completion of the regioselective hydrodebromination contains no more than about 1 wt % (preferably no more than about 0.5 wt %) of non-brominated 2-naphthol, and no more than about 5 wt % (preferably no more than about 1 wt %) of ar-polybromo impurities. Most preferably the recovered 6-bromo-2-naphthol product on completion of the regioselective hydrodebromination contains no more than about 0.5 wt % of non-brominated impurities, and no more than about 1 wt % of polybromo impurities.

The best way of performing the controlled purge of by-product hydrogen bromide from the reaction mixture is to sparge the reaction mixture with hydrogen throughout substantially the entire hydrodebromination reaction period. In this operation the hydrogen should be continuously introduced into the lowermost portion of the reaction mixture so that it sweeps through substantially the entire reaction mixture and the resultant vapors should be continuously removed from the headspace above the reaction mixture at a rate sufficient to keep the gaseous input to and output from the reaction in a substantially equilibrium condition. Thus, reactors equipped with sparger inlets at their lower interiors and gaseous offtake outlets at their upper interiors are preferably employed. The gaseous mixture of hydrogen and entrained hydrogen bromide is preferably passed through a scrubber system containing water and/or a suitable base, e.g., aqueous sodium hydroxide, to remove the hydrogen bromide from the hydrogen so that the hydrogen can be recycled continuously in the purging operation.

Thus, a preferred way of producing 6-bromo-2-naphthol pursuant to this invention is a process that comprises reacting 1,6-dibromo-2-naphthol with hydrogen or a precursor compound that generates nascent hydrogen in the medium of the reaction, in a halogen-containing liquid solvent comprising at least about 50% (most preferably over 95%) by weight of (a) at least one liquid organic halide solvent in which the halogen content has an atomic number of 35 or less (especially ethylene dichloride) or (b) a solvent mixture consisting essentially (e.g., at least about 90% and most preferably over 98%) by weight of the combination of water and at least one such liquid organic halide solvent (especially ethylene dichloride), and in the presence of catalytically effective amounts of (i) a tungsten carbide-based catalyst, and (ii) at least one phase transfer catalyst, and in the presence at the start of the reaction of a small, reaction-initiating amount of an acid, preferably a carboxylic acid or more preferably, a mineral acid or anhydride, most preferably hydrobromic acid or hydrogen bromide, such that 6-bromo-2-naphthol is formed, and substantially continuously purging hydrogen bromide from the reaction mixture substantially as soon as it is formed.

The regiospecific hydrodebromination reaction when conducted with purge of hydrogen bromide from the reaction mixture is typically conducted at temperatures in the range of about 50° to about 150° C. at pressures in the range of about 65 to about 200 psig, and preferably at temperatures in the range of about 90° to about 120° C. at pressures in the range of about 65 to about 120 psig.

If a purge of hydrogen bromide is not used, the only presently known way of achieving satisfactory results is to perform the reaction at relatively high temperatures and pressures (e.g., 100° to 300° C. at 500 to 1500 psig).

Upon completion of the regioselective hydrodebromination reaction, the organic halide solvent is removed from the 6-bromo-2-naphthol formed in the reaction so that the 6-bromo-2-naphthol is at least substantially completely free from any halogen-containing impurity content. A preferred way of effecting this separation involves (i) adjusting the pH of the reaction mixture to approximately 7 to thereby prevent or at least markedly suppress isomerization or disproportionation of the product(s) in the reaction mixture, (ii) distilling off most of the organic halide solvent from the reaction mixture, (iii) adding water to the reaction mixture, and then (iv) distilling off the remainder of the organic halide solvent azeotropically with water, and keeping the temperature of the reaction mixture below 100° C. when conducting each of these operations. This method has proven exceptionally effective when using ethylene dichloride as the organic halide of the liquid reaction medium. As those skilled in the art can readily appreciate, the initial amount of organic halide distilled off, and the amount of water added to the residual mixture for use in conducting the azeotropic distillation are largely discretionary, involve the use of common sense, and can be readily optimized for any given set of circumstances. As a point of reference, if the liquid reaction medium is composed solely of ethylene dichloride, the initial distillation will typically remove from 85 to 95 percent of the ethylene dichloride, and the amount of water added will typically be about 10 to about 20 wt % of the original ethylene dichloride, or about 80 to about 120 wt % of the ethylene dichloride remaining in the reaction product.

To illustrate preferred procedures for conducting the regioselective hydrodebromination reaction in accordance with this invention, the following non-limiting examples are presented. In these examples four basic general procedures were used. In Examples 8–14 (Table 1) catalytic hydrodebromination was conducted per this invention using tungsten carbide catalyst and a phase transfer co-catalyst without purge of hydrogen bromide. Examples 15–48 (Table 2) were catalytic hydrodebromination reactions conducted per preferred embodiments of this invention using tungsten carbide catalyst, a phase transfer co-catalyst and continuous purge of hydrogen bromide from the reaction mixture during the reaction. Comparative Examples 49–51 (Table 3) and Comparative Examples 52–55 (Table 4) show results achieved when hydrodebromination reactions were conducted using tungsten carbide catalyst but without phase transfer catalyst, and where in Table 3 no purge of hydrogen bromide was used and Table 4 where a purge of hydrogen was used during the reaction.

EXAMPLES 8–14

The general procedure for catalytic hydrodebromination using tungsten carbide catalyst and a phase transfer co-catalyst without purge of hydrogen bromide (Table 1) is as follows: The reactions were conducted in either a 100 or 300 mL Hastalloy B autoclave. For addition of hydrogen, the reactor was equipped with an incoming line to the interior of the reactor, and dip tube therein. Hydrogen pressure was controlled by means of a regulator valve at the gas cylinder. Contents of the reactor were agitated either at 680 rpm or 1700 rpm throughout the reaction. A solution of 1,6-dibromo-2-naphthol (1,6-DBN) in ethylene dichloride (EDC), tungsten carbide catalyst (with average particle size of less than 1 micron) and tetrabutylammonium bromide (TBAB) or in some cases, cetyltrimethylammonium bromide (CTAB) co-catalyst were charged to the reactor. The reactor was then sealed and purged three times with hydrogen. Next, the reactor was pressurized with hydrogen and slowly warmed to the desired reaction temperature. Hydrogen was added as necessary to maintain the pressure at the desired level. Samples were withdrawn periodically to monitor progress of the reaction. At the end of the reaction, the reaction mixture was allowed to settle and the organic layer was decanted or removed through the dip tube. The tungsten carbide catalyst was either used for a second run or washed with solvent and discarded. Conditions and results of representative runs conducted in this manner are summarized in Table 1. Unless otherwise indicated, in each run of Table 1, (a) the tungsten carbide catalyst concentration was 10 wt %, (b) 2.41 grams of 1,6-DBN in 60 mL of EDC (an approximately 0.13 molar solution) was charged to the reactor along with 0.1–0.2 wt % of the co-catalyst, (c) the co-catalyst was TBAB, and (d) reaction was conducted at 500 psig with stirring at 680 rpm. Each example is a single continuous run with analytical results shown on samples withdrawn after various times specified cumulatively in the table. To illustrate, Example 8 was run for 4 hours with samples taken at the end of 0.5, 1, 2, 3, and 4 hours, and conditions were held constant throughout, except that at the start of the 3rd hour of the run the temperature was raised from 100° C. to 125° C. and held there for the next one hour.

In the tables. 8-BN is 8-bromonaphthol and 2-NTL is 2-naphthol.

TABLE 1

Hydrodebromination With WC and Phase Transfer Catalysts Without Hbr Purge

| Ex. No. | Temp., °C. | Time, hr | 1,6-DBN, % | 6-BN, % | Others, % | Comments |
|---|---|---|---|---|---|---|
| 8 | 100 | 0.5 | 91.7 | 8.2 | none | (1) |
|  | 100 | 1 | 80.2 | 19.6 | none |  |
|  | 100 | 2 | 60.4 | 33.8 | none |  |
|  | 100 | 3 | 53.0 | 42.1 | none |  |
|  | 125 | 4 | 16.4 | 45.7 | 2-NTL, 18.8 |  |
| 9 | 110 | 1 | 36.5 | 52.6 | 2-NTL, 2.0 | (1) |
|  | 110 | 2 | 14.3 | 52.6 | 2-NTL, 16.3 |  |
|  | 110 | 3 | 8.2 | 44.5 | 2-NTL, 35.7 |  |
| 10 | 105 | 0.5 | 67.5 | 30.5 |  | (1) |
|  | 105 | 1 | 50.6 | 43.6 | 2-NTL, 0.6 |  |
|  | 105 | 1.5 | 39.9 | 48.7 | 2-NTL, 4.8 |  |
|  | 105 | 2 | 28.9 | 51.9 | 2-NTL, 10.4 |  |
|  | 105 | 2.5 | 20.3 | 52.9 | 2-NTL, 15.7 |  |
|  | 105 | 3 | 13.4 | 52.9 | 2-NTL, 22.5 |  |
| 11 | 103 | 0.5 | 40.9 | 59.1 | none | (1), (2) |
|  | 103 | 1 | 18.1 | 80.9 | none |  |
|  | 103 | 1.5 | 10.0 | 88.9 | none |  |
|  | 103 | 2 | 5.5 | 90.7 | none |  |
|  | 103 | 2.5 | 1.4 | 88.3 | 2-NTL, 4.4 |  |
| 12 | 103 | 0.5 | 40.8 | 54.3 | none | (1), (3) |
|  | 103 | 1 | 19.5 | 73.5 | 2-NTL, 1.8 |  |
|  | 103 | 1.5 | 11.0 | 78.8 | 2-NTL, 5.0 |  |
|  | 103 | 2 | 6.8 | 78.5 | 2-NTL, 10.2 |  |
|  | 103 | 2.5 | 4.3 | 76.9 | 2-NTL, 15.1 |  |
| 13 | 130 | 5 | 0.7 | 67.6 | 2-NTL, 25.8; others, 5.9 | (1), (4) |
| 14 | 110 | 2.5 | 1.5 | 81.3 | 2-NTL, 6.4; other, 10.8 | (1), (4) |

(1) The amount of Hbr at the start of the reaction was not measured; However, the initial EDC solvent was saturated with or at least contained sufficient Hbr to initiate the reaction.
(2) In this example, the starting solution was 18 wt % of 1,6-DBN in EDC.
(3) In this example, the starting solution was 29 wt % of 1,6-DBN in EDC.
(4) In this example, 20 wt % of tungsten carbide catalyst, a 30 wt % solution of 1,6-DBN in EDC, and 0.2 gram of CTAB co-catalyst were used; the pressure was 250 psig and the mixture was stirred at 1700 rpm.

EXAMPLES 15–48

In the examples given in Table 2, the general procedure of the examples of Table 1 was used except that pursuant to a preferred embodiment of this invention this catalytic hydrodebromination with tungsten carbide and phase transfer catalysts was conducted with a continuous purge of hydrogen bromide from the reactor throughout the reaction. Hydrogen was used as the purging gas and the purge stream of off-gases from the reaction was passed into a caustic scrubber, while keeping the internal pressure in the reactor at the desired level by the continuous introduction of fresh hydrogen. For effecting the purge, a valve was connected to the head-space of the reactor. Connected to this valve was ¼-inch polytetrafluoroethylene tubing which directed the purge stream through a knockout pot and thence into two 20 wt % caustic solutions arranged in series. After the gas passed through the scrubbers, it was passed through a wet test meter filled with Varsol. Readings from the wet test meter were recorded to control the incoming flow of fresh hydrogen into the reactor.

TABLE 2

Hydrodebromination With WC and Phase Transfer Catalysts and With Hbr Purge

| Ex. No. | DBN, wt % | WC, wt % | Co-catalyst, wt % | Temp. °C. | Pressure, psig | Time, hr | 1,6-DBN, % | 6-BN, % | Others, % | Comments |
|---|---|---|---|---|---|---|---|---|---|---|
| 15 | 30 | 20 | CTAB, 1.5 | 100 | 90 | 6 | 0.2 | 88.5 | 2-NTL, 2.6 |  |
| 16 | 30 | 20 | CATB, 2 | 100 | 90 | 5 | 0.3 | 82 | 2-NTL, 6.5 |  |
| 17 | 30 | 17 | TBAB, 2 | 100 | 90 | 7 | 0.6 | 83.5 | 2-NTL, 10.3 |  |
| 18 | 30 | 17 | TBAB, 1 | 110 | 90 | 5 | 0.2 | 87.7 | 2-NTL, 5.1 |  |
| 19 | 33 | 20 | TBAB, 0.5 | 115 | 90 | 5 | 0.3 | 89.6 | 2-NTL, 2.7 |  |
| 20 | 33 | 20 | TBAB, 0.2 | 115 | 90 | 6 | 0.6 | 91 | 2-NTL, 1.1 |  |
| 21 | 30 | 20 | TBAB, 0.25 | 115 | 95 | 5.5 | 0.6 | 94.7 | 2-NTL, 1.5 |  |
| 22 | 34 | 20 | TBAB, 0.1 | 115 | 62 | 7 | 0.4 | 91.3 | 2-NTL, 0.3 |  |
| 23 | 34 | 30 | TBAB, 0.1 | 115 | 63 | 6 | 0.1 | 88 | 2-NTL, 0.7 | (1) 1.6 |
| 24 | 34 | 30 | TBAB, 0.1 | 125 | 125 | 2 | 0.5 | 83 | 2-NTL, 3.7 | (1) 2.3 |
| 25 | 44 | 20 | TBAB, 0.1 | 115 | 300 | 2 | 0.4 | 55 | 2-NTL, 21.2 | (1) 14.8, (7) |
| 26 | 34 | 20 | TBAB, 0.1 | 115 | 300 | 2 | 0.2 | 81.8 | 2-NTL, 4.6 | (1) 4.2 |
| 27 | 34 | 20 | TBAB, 0.1 | 115 | 300 | 2 | 0.1 | 88 | 2-NTL, 2.7 | (1) 2.1 |
| 28 | 34 | 30 | TBAB, 0.1 | 90 | 125 | 4.5 | 0.4 | 84.2 | 2-NTL, 3.2 |  |
| 29 | 34 | 30 | TBAB, 0.1 | 90 | 125 | 5.5 | 0.4 | 90.2 | 2-NTL, 0.5 | (7) |
| 30 | 44 | 30 | TBAB, 0.1 | 90 | 125 | 4 | 0.5 | 88.6 | 2-NTL, 1.3 | (7) |
| 31 | 33 | 30 | TBAB, 0.1 | 90 | 125 | 7 | 2.8 | 84.6 | 2-NTL, 1.0 | (7) |
| 32 | 33 | 30 | TBAB, 0.1 | 90 | 125 | 6 | 0.6 | 89.5 | 2-NTL, 1.7 | (7) |
| 33 | 33 | 30 | TBAB, 0.1 | 90 | 125 | 6 | 1.2 | 85.3 | 2-NTL, 1.5 | (2), (7) |
| 34 | 34 | 30 | TBAB, 0.1 | 90 | 125 | 4 | 2.1 | 54.4 | 2-NTL, 21.5 | (3), (7) |
| 35 | 38 | 30 | TBAB, 0.1 | 90 | 125 | 8 | 1.3 | 77.9 | 2-NTL, 0.6 | (4) |
| 36 | 33 | 30 | TBAB, 0.1 | 90 | 125 | 1.5 | 3.4 | 76.9 | 2-NTL, 6.4 | (5), (7) |
| 37 | 33 | 30 | TBAB, 0.1 | 90 | 125 | 2 | 1.1 | 83.2 | 2-NTL, 3.2 | (5), (7) |
| 38 | 33 | 30 | TBAB, 0.1 | 115 | 125 | 2 | 0.4 | 85.3 | 2-NTL, 1.5 | (7) |
| 39 | 33 | 30 | TBAB, 0.1 | 115 | 125 | 3.5 | 0.6 | 87.8 | 2-NTL, 0.5 | (7) |
| 40 | 33 | 30 | TBAB, 0.1 | 115 | 125 | 1 | 0.7 | 85.2 | 2-NTL, 4.0 | (7) |
| 41 | 33 | 30 | TBAB, 0.1 | 115 | 127 | 3 | 0.3 | 86.9 | 2-NTL, 2.1 | (7) |
| 42 | 33 | 30 | TBAB, 0.1 | 115 | 127 | 3 | 0.3 | 88.5 | 2-NTL, 0.5 | (7) |
| 43 | 33 | 30 | TBAB, 0.1 | 115 | 127 | 3 | 56.6 | 33.7 | 2-NTL, 0.1 | (7) |

TABLE 2-continued

Hydrodebromination With WC and Phase Transfer Catalysts and With Hbr Purge

| Ex. No. | DBN, wt % | WC, wt % | Co-catalyst, wt % | Temp. °C. | Pressure, psig | Time, hr | 1,6-DBN, % | 6-BN, % | Others, % | Comments |
|---|---|---|---|---|---|---|---|---|---|---|
| 44 | 33 | 30 | TBAB, 0.1 | 115 | 127 | 3 | 0.3 | 89.3 | 2-NTL, 1.4 | (7) |
| 45 | 33 | 30 | TBAB, 0.1 | 115 | 127 | 1 | 3.8 | 82.6 | 2-NTL, 3.5 | (6), (7) |
| 46 | 34 | 30 | TBAB, 0.1 | 115 | 127 | 1 | 0.3 | 90.6 | 2-NTL, 6.1 | (7) |
| 47 | 34 | 30 | TBAB, 0.1 | 115 | 127 | 0.5 | 0.6 | 87.4 | 2-NTL, 1.1 | (7) |
| 48 | 33 | 30 | TBAB, 0.1 | 115 | 93 | 3 | 0.5 | 87.1 | 2-NTL, 2.4 | (7) |

(1) Other impurities were detected in the amount shown.
(2) 48% Hbr was added before the start of the reaction.
(3) Anhydrous Hbr was added before the start of the reaction.
(4) Additional EDC was added during the reaction as makeup for purged EDC.
(5) The reactor was vented during the reaction.
(6) Acetic acid was added to the initial solution of 1,6-DBN in EDC to initiate the reaction.
(7) The solvent used was a mixture of EDC and water

COMPARATIVE EXAMPLES 49–55

Except as otherwise indicated in Tables 3 and 4, the comparative runs summarized therein were conducted in comparable manner to those of Tables 1 and 2 except that the runs of Table 3 had no transfer catalyst and no purge of Hbr whereas the runs of Table 4 did have Hbr purge but no phase transfer catalyst.

Three-Stage Process for Producing 2-Bromo-6-Methoxynaphthalene

A preferred synthesis process for producing 2-bromo-6-methoxynaphthalene in accordance with this invention involves three main reactions, together with particular separation and purification procedures. A detailed procedure for performing this operation is as follows: A first step

TABLE 3

Hydrodebromination With WC but Without Phase Transfer Catalyst and Without Hbr Purge

| Ex. No. | Hbr, g | Temp., °C. | Time, hr | 1,6-DBN, % | 6-BN, % | Others, % | Comments |
|---|---|---|---|---|---|---|---|
| 49 | 0.64 | 150 | 1 | 93.4 | 6.6 | none | (1) |
|    |      | 150 | 3 | 83.8 | 16.2 | none |  |
|    |      | 150 | 4 | 46.0 | 54.0 | none |  |
|    |      | 250 | 5.5 | 19.8 | 75.2 | 8-BN, 5.0 |  |
| 50 |      | 150 | 0.5 | 59.3 | 40.5 |  | (2), (3) |
|    |      | 150 | 1 | 35.8 | 64.2 | 2-NTL, 1.5 |  |
|    |      | 150 | 2 | 14.9 | 81.6 | 2-NTL, 2.6 |  |
|    |      | 150 | 3 | 3.9 | 82.6 | 2-NTL, 7.2 |  |
|    |      | 150 | 4 | 1.5 | 83.1 | 2-NTL, 14.8 |  |
| 51 |      | 100 | 0.5 | 73.9 | 20.8 | 2-NTL, 5.3 | (2), (4) |
|    |      | 100 | 1 | 55.7 | 38.7 | 2-NTL, 5.7 |  |
|    |      | 100 | 1.5 | 37.2 | 55.9 | 2-NTL, 7.0 |  |
|    |      | 100 | 2 | 22.2 | 69.3 | 2-NTL, 2.0 |  |
|    |      | 100 | 2.5 | 10.8 | 77.6 | 2-NTL, 4.7 |  |
|    |      | 100 | 3 | 5.5 | 78.4 | 2-NTL, 7.9 |  |
|    |      | 100 | 3.5 | 2.1 | 70.1 | 2-NTL, 12.2 |  |
|    |      | 100 | 4 | 2.0 | 70.1 | 2-NTL, 9.1 |  |

(1) In this example, 48% aqueous Hbr was added to the initial solution of 1,6-DBN in EDC.
(2) The amount of Hbr at the start of the reaction was not measured; However, the initial ED solvent was saturated or at least contained sufficient Hbr to initiate the reaction.
(3) In this example, the starting solution was 29 wt % of 1,6-DBN in EDC.
(4) In this example, 108 mL of EDC was used as the solvent/diluent.

TABLE 4

Hydrodebromination With WC and With Purge but Without Phase Transfer Catalyst

| Ex. No. | DBN, wt % | Solvent | WC, wt % | Temp. °C. | Pressure, psig | Time, hr | 1,6-DBN, % | 6-BN, % | Others, % |
|---|---|---|---|---|---|---|---|---|---|
| 52 | 34 | EDC | 20 | 110 | 62 | 5 | 57.1 | 32.3 | 2-NTL, 0.1 |
| 53 | 44 | EDC/H$_2$O | 20 | 115 | 300 | 1.5 | 0.6 | 58.2 | 2-NTL, 20.1 |
| 54 | 33 | EDC/H$_2$O | 15 | 90 | 125 | 3 | 9.4 | 75.0 | 2-NTL, 2.4 |
| 55 | 33 | EDC/H$_2$O | 30 | 115 | 127 | 3.5 | 0.8 | 80.5 | 2-NTL, 7.2 |

(assuming 1,6-dibromo-2-naphthol of suitable purity is not commercially available at an attractive price) involves forming 1,6-dibromo-2-naphthol by brominating 2-naphthol in ethylene dichloride, or in a mixture of ethylene dichloride (EDC) and water using a phase transfer catalyst such as described in U.S. Pat. No. 5,426,243. On completion of the reaction the aqueous phase is separated from the organic phase by decantation. Then tungsten carbide of about 0.9 micron average particle size (about 6 to 12 wt % of the total weight of the resulting mixture) and TBAB (about 0.02 to 0.05 wt % based on the total weight of the resulting mixture) are added to the organic phase. This mixture is then selectively hydrodebrominated with continuous hydrogen purge at 60 to 90 psig at 100° C. to 110° C. for 4 to 8 hours with constant agitation of the reaction mixture to ensure intimate contact among the three phases in the system. Then the reaction product mixture is allowed to stand long enough for the solids to settle, and the liquid phase is separated from the solids by decantation. The EDC solution is then neutralized with aqueous caustic solution. Most of the EDC is flashed off or removed by distillation, water is added to the product residue, and the remainder of the EDC is removed therefrom by azeotropic distillation with water. 2-Propanol is added to the EDC-freed, molten 6-bromo-2-naphthol product residue in proportions by weight of about 3:1, respectively. Next, sodium hydroxide (about 10 mole% excess based on 6-bromo-2-naphthol) and methyl chloride (about 20 mole % excess relative to 6-bromo-2-naphthol) are charged to the reactor containing the 2-propanol and EDC-freed product mixture. The resultant mixture is heated to about 70° to about 90° C. for about 3 to about 5 hours with constant agitation. Then the 2-propanol is stripped off, and the residue while hot enough to keep the 2-bromo-6-methoxynaphthalene in molten condition (e.g., 90° to 112° C.) is washed with water (under superatmospheric pressure, if necessary) and the washings are discarded. The washed product is then subjected to distillation (about 160° to 165° C. at 1 mmhg) to recover purified 2-bromo-6-methoxynaphthalene. Then the purified 2-bromo-6-methoxynaphthalene is dissolved in and crystallized from 2-propanol at 10° C. to yield 2-bromo-6-methoxynaphthalene in highly purified, white crystalline form.

Production of (±)-2-(6-Methoxy-2-Naphthyl) Propionic Acid and Precursors Thereof (A) Preparation of Grignard Reagent of 2-Bromo-6-Methoxynaphthalene. a Precursor of (±)-2-(6-Methoxy-2-Naphthyl)Propionic Acid One embodiment of this invention comprises preparing 2-bromo-6-methoxynaphthalene as described herein and then converting the 2-bromo-6-methoxynaphthalene into a Grignard reagent by reaction with magnesium in a suitable anhydrous liquid reaction medium in a suitably inert atmosphere (dry nitrogen, argon, helium, etc.). The reaction is typically conducted in an ethereal and/or inert hydrocarbon reaction medium at one or more temperatures in the range of about 0° C. to about 110° C. with agitation for a time sufficient to cause reaction such that the Grignard reagent (2-(6-methoxynaphthyl)magnesium bromide), a precursor of (±)-2-(6-methoxy-2-naphthyl)propionic acid is formed. Substantially complete reaction normally occurs in the range of from about 0.1 to about 6 hours. In accordance with one suitable procedure, the Grignard reagent can be formed by adding finely divided magnesium and, optionally a crystal of iodine, to a solution of 2-bromo-6-methoxynaphthalene in a suitable ether, such as diethyl ether or tetrahydrofuran in a dry, inert environment, and stirring the mixture at a temperature in the range of about 25° to about 80° C. Alternatively the 2-bromo-6-methoxynaphthalene can be added portionwise to a two-phase mixture of magnesium in the form of turnings or other subdivided condition in an anhydrous liquid reaction diluent such as a liquid ether or hydrocarbon under an inert atmosphere, while agitating the resultant reaction mixture at one or more selected reaction temperatures. Another procedure is to slowly mix together under an inert atmosphere, the dry magnesium metal and a solution of the 2-bromo-6-methoxynaphthalene in a suitable medium such as an ether or an inert hydrocarbon, or a mixture thereof, and agitate the mixture while heating to one or more suitable reaction temperatures. The following Examples 56–60 serve to illustrate suitable procedures for conducting this reaction. Examples 56–59 are based in part on procedures described in U.S. Pat. Nos. 3,663,584 (May 16, 1972) to F. Alvarez; 3,658,858 (Apr. 25, 1972) to I. T. Harrison; 3,959,364 (May 25, 1976) to B. J. Armitage, J. E. Jeffery, J. S. Nicholson and J. G. Tantum; and 4,144,397 (Mar. 13, 1979) to G. J. Matthews and R. A. Arnold, respectively, the entire disclosures of which are incorporated herein by reference. Example 60 is based in part on the procedure of A. Horeau, J. Jacques and R. Émiliozzi, *Bull. Soc. Chim. Fr.* 1959, at page 1857.

EXAMPLE 56

A mixture of 2-bromo-6-methoxynaphthalene prepared as in Example 7 hereof (11.3 grams) in 30 mL of benzene is slowly added to 1.2 grams of magnesium turnings in 20 mL of benzene at reflux temperature under nitrogen. The product is a benzene solution of the Grignard reagent generally named as 2-(6-methoxynaphthyl)magnesium bromide.

EXAMPLE 57

A solution is formed by dissolving 24 grams of 2-bromo-6-methoxynaphthalene prepared as in Example 7 hereof in 300 mL of tetrahydrofuran. This solution is slowly added to a stirred mixture of 2.5 grams of magnesium turnings in 100 mL of tetrahydrofuran at reflux temperature. The reaction, performed under anhydrous reaction conditions, yields a tetrahydrofuran solution of the Grignard reagent, 2-(6-methoxynaphthyl)magnesium bromide.

EXAMPLE 58

A solution is formed from 2-bromo-6-methoxynaphthalene (2.37 grams, 0.01 mol), prepared as in Example 7 hereof, and 15 mL of dry tetrahydrofuran. The resultant solution is added dropwise with stirring to magnesium turnings (0.25 gram; 0.0103 gram atom) under a nitrogen atmosphere. When the addition is complete, the mixture is stirred and boiled under reflux for 30 minutes, and then cooled to room temperature. The product of this reaction is a solution of the Grignard reagent in tetrahydrofuran.

EXAMPLE 59

2-Bromo-6-methoxynaphthalene (23.7 grams; 0.1 mol) prepared as in Example 7 hereof is dissolved in a mixture of toluene (30 mL) and tetrahydrofuran (40 mL) with heating. This solution is then added over a 10–15 minute period to an excess of magnesium metal (3 grams; 0.12 mol) in a mixture of toluene (15 mL) and tetrahydrofuran (15 mL) under a nitrogen atmosphere. After cooling the reaction mixture to 25°–30° C., the reaction mixture is stirred for an additional hour at 25°–30° C. and then transferred away from the excess magnesium to a clean, dry vessel under nitrogen and stored at 10° C. to afford a 1.0M Grignard reagent.

By utilizing less solvent in the procedure of Example 59, a more concentrated Grignard reagent, e.g., 1.5M, may be prepared.

EXAMPLE 60

To a reactor equipped with a stirrer are charged 10 grams of 2-bromo-6-methoxynaphthalene prepared as in Example 7 hereof, 1.05 grams of magnesium and 35 mL of tetrahydrofuran (THF). The reaction is initiated by addition of a crystal of iodine. The reaction mixture is then heated for one hour at reflux with stirring to form a solution of the Grignard reagent in THF.

(B) Preparation of Bis(6-Methoxy-2-Naphthyl)Zinc, (6-Methoxy-2-Naphthyl)Zinc Halide or Mixtures Thereof, Precursors of (±)-2-(6-Methoxy-2-Naphthyl)Propionic Acid In this embodiment the Grignard reagent formed as in (A) above is reacted with zinc halide (chloride, bromide or iodide or mixture of any two or all three of these zinc halides) in a suitable solvent such as an inert hydrocarbon solvent such as one or more liquid aromatic hydrocarbons (benzene, toluene, xylene, etc.) at one or more suitable reaction temperatures, which are typically, but not necessarily, in the range of about 20° to about 80° C. The proportions of these reactants used largely determines whether the product is bis(6-methoxy-2-naphthyl)zinc, (6-methoxy-2-naphthyl)zinc halide (chloride, bromide, iodide), or a mixture of bis(6-methoxy-2-naphthyl)zinc and such (6-methoxy-2-naphthyl)zinc halide. Thus, if one-half molar equivalent of zinc halide relative to the Grignard reagent is employed, the product is primarily bis(6-methoxy-2-naphthyl)zinc whereas if one molar equivalent of zinc halide relative to the Grignard reagent is employed, the product is primarily (6-methoxy-2-naphthyl)zinc halide. By using proportions of zinc halide between 1 and 0.5 equivalents, it is possible to form various mixtures of bis(6-methoxy-2-naphthyl)zinc and (6-methoxy-2-naphthyl) zinc halide. Suitable procedures which may be used in the practice of this embodiment are described in U.S. Pat. No. 3,663,584 (May 16, 1972) to F. Alvarez upon which the following Examples 61–65 are, in part, based, and the entire disclosure of which has been, and is hereby again, incorporated herein by reference.

EXAMPLE 61

To the solution of Grignard reagent in 50 mL benzene formed in Example 56 above under nitrogen is added 3.14 grams of anhydrous zinc chloride. The temperature of the resultant mixture is maintained at temperatures of 25° to 30° C. for one hour with constant stirring. Formed is a benzene solution of bis(6-methoxy-2-naphthyl)zinc. When this procedure is repeated at 50° C. using one equivalent of zinc bromide, the product is primarily a benzene solution of (6-methoxy-2-naphthyl)zinc bromide.

EXAMPLE 62

One equivalent of zinc chloride is mixed with one equivalent of Grignard reagent formed pursuant to this invention as in Example 57 above wherein the 2-bromo-6-methoxynaphthalene used is prepared as in Example 7 above. The resultant mixture is maintained at 25° to 30° C. for one hour with constant stirring. Formed is a tetrahydrofuran solution containing 6-methoxy-2-naphthylzinc chloride. In another operation, this procedure is repeated at 50° C. using 0.5 equivalent of zinc bromide instead of one equivalent of zinc chloride. In this case the product is primarily a tetrahydrofuran solution of bis(6-methoxy-2-naph

EXAMPLE 63

The two operations of Example 62 are repeated in the same way except that the Grignard reagent used is formed pursuant to this invention as in Example 58 above using 2-bromo-6-methoxynaphthalene prepared as in Example 7 above.

EXAMPLE 64

The two operations of Example 62 are repeated in the same way except that the Grignard reagent used is formed pursuant to this invention as in Example 59 above. The two respective products formed in this instance are solutions of 6-methoxy-2-naphthylzinc chloride and bis(6-methoxy-2-naphthyl)zinc, each in a mixed solvent composed of tetrahydrofuran and toluene.

EXAMPLE 65

The two operations of Example 62 are repeated in the same way except that the Grignard reagent used is formed pursuant to this invention as in Example 60 above.

(C) Preparation of Bis(6-Methoxy-2-Naphthyl) Cadmium, (6-Methoxy-2-Naphthyl)Cadmium Halide or Mixtures Thereof, Precursors of (±)-2-(6-Methoxy-2-Naphthyl)Propionic Acid In this embodiment the Grignard reagent formed as in (A) above is reacted with cadmium halide (chloride, bromide or iodide or mixture of any two or all three of these cadmium halides) in a suitable solvent such as an inert hydrocarbon solvent such as one or more liquid aromatic hydrocarbons (benzene, toluene, xylene, etc.) at one or more suitable reaction temperatures, which are typically, but not necessarily, in the range of about 20° to about 80° C. The proportions of these reactants used largely determines whether the product is bis(6-methoxy-2-naphthyl)cadmium, (6-methoxy-2-naphthyl)cadmium halide (chloride, bromide, iodide), or a mixture of bis(6-methoxy-2-naphthyl)cadmium and such (6-methoxy-2-naphthyl)cadmium halide. Thus, if one-half molar equivalent of cadmium halide relative to the Grignard reagent is employed, the product is primarily bis(6-methoxy-2-naphthyl)cadmium whereas if one molar equivalent of cadmium halide relative to the Grignard reagent is employed, the product is primarily (6-methoxy-2-naphthyl)zinc halide. By using proportions of zinc halide between 1 and 0.5 equivalents, it is possible to form various mixtures of bis(6-methoxy-2-naphthyl)zinc and (6-methoxy-2-naphthyl)zinc halide. Suitable procedures which may be used in the practice of this embodiment are described in U.S. Pat. Nos. 3,658,858 (Apr. 25, 1972) to I. T. Harrison and 3,694,476 (Sep. 26, 1972) to F. Alvarez upon which the following Examples 66–70 are, in part, based, and the entire disclosures of which are hereby incorporated herein by reference.

EXAMPLE 66

To the solution of Grignard reagent in 50 mL benzene formed as in Example 56 above, and under nitrogen is added 4.59 grams of anhydrous cadmium chloride. The temperature of the resultant mixture is maintained at temperatures of 20° to 30° C. for one hour with constant stirring. Formed is a benzene solution of bis(6-methoxy-2-naphthyl)cadmium. When this procedure is repeated at 50° C. using one equivalent of anhydrous cadmium bromide, the product is primarily a benzene solution of (6-methoxy-2-naphthyl)cadmium bromide.

EXAMPLE 67

The procedure of Example 57 above is repeated to form Grignard reagent pursuant to this invention from 2-bromo-6-methoxynaphthalene prepared as in Example 7 above. One equivalent of cadmium chloride is mixed with one equivalent of the resultant tetrahydrofuran solution of the Grignard reagent under inert, anhydrous conditions. This reaction mixture is refluxed for 30 minutes to form a tetrahydrofuran solution containing 6-methoxy-2-naphthylcadmium chloride. In another operation, this procedure is repeated at 50° C. using 0.5 equivalent of anhydrous cadmium bromide instead of one equivalent of cadmium chloride. In this case the product is primarily a tetrahydrofuran solution of bis(6-methoxy-2-naphthyl)cadmium.

EXAMPLE 68

The two operations of Example 67 are repeated in the same way except that the Grignard reagent used is formed pursuant to this invention as in Example 58 above.

EXAMPLE 69

The two operations of Example 67 are repeated in the same way except that the Grignard reagent used is formed pursuant to this invention as in Example 59 above. The two respective products formed in this instance are solutions of 6-methoxy-2-naphthylcadmium bromide and of bis(6-methoxy-2-naphthyl)cadmium, each in a mixed solvent composed of tetrahydrofuran and toluene.

EXAMPLE 70

The two operations of Example 67 are repeated in the same way except that the Grignard reagent used is formed pursuant to this invention as in Example 60 above.

(D) Preparation of 6-Methoxy-2-NaphthylLithium, a Precursor of (±)-2-(6-Methoxy-2-Naphthyl) Propionic Acid Another embodiment of this invention comprises preparing 2-bromo-6-methoxynaphthalene as described herein, and converting the 2-bromo-6-methoxynaphthalene into 6-methoxy-2-naphthyllithium, another versatile intermediate which can be used for producing, inter alia, 6-methoxy-2-naphthylcopper(I), another precursor of (±)-2-(6-methoxy-2-naphthyl)propionic acid. The lithium reagent is formed by mixing 2-bromo-6-methoxynaphthalene with lithium metal in a suitable liquid reaction medium such as an anhydrous ethereal medium. The reaction is typically, but not necessarily, conducted at temperatures in the range of about 20° to about 50° C. Preferably the reactants are mixed together slowly, as by adding small portions of one to the other while in a suitable continuously stirred liquid reaction medium. Example 71 below is based in part on the procedure U.S. Pat. No. 3,658,863 (Apr. 25, 1972) to I. T. Harrison, the entire disclosure of which is incorporated herein by reference.

EXAMPLE 71

A solution is formed from 23 grams of 2-bromo-6-methoxynaphthalene prepared as in Example 7 above, and 100 mL of tetrahydrofuran. The solution is slowly added to 1.4 grams of lithium metal in 100 mL of tetrahydrofuran with stirring at ambient temperature until the reaction is complete as evidenced by disappearance of substantially all lithium metal particles from the reaction solution. The resultant product solution is comprised of 6-methoxy-2-naphthyllithium dissolved in tetrahydrofuran.

(E) Preparation of 6-Methoxy-2-Naphthylcopper(I), a Precursor of (±)-2-(6-Methoxy-2-Naphthyl) Propionic Acid In this embodiment a cuprous halide such as cuprous chloride, bromide or iodide is mixed with a solution of 6-methoxy-2-naphthyllithium in a suitable anhydrous liquid solvent such as an ether, which solution is prepared as in (D) above. The resultant mixture is stirred under an inert atmosphere for a period of time, typically from 1 to 2 hours, sufficient for the formation of a solution containing 6-methoxy-2-naphthylcopper(I). The reaction is typically, but not necessarily, conducted at temperatures in the range of about 15° to about 25° C. If desired, the 6-methoxy-2-naphthylcopper(I) can be isolated by removing the ether solvent under vacuum while maintaining the solution temperature below about 30° C. The product, if isolated in this manner and if not used promptly, should be stored in a sealed container in an anhydrous inert atmosphere and at room temperature or below. The following Example 72 is based in part on the procedure U.S. Pat. No. 3,658,863 (Apr. 25, 1972) to I. T. Harrison, the entire disclosure of which has been incorporated herein by reference.

EXAMPLE 72

A solution is formed from 23 grams of 2-bromo-6-methoxynaphthalene prepared as in Example 7 above, and 100 mL of tetrahydrofuran. The solution is slowly added to 1.4 grams of lithium metal in 100 mL of tetrahydrofuran with stirring at ambient temperature until the reaction is complete as evidenced by the disappearance of substantially all lithium metal particles from the reaction solution. The resultant product solution is comprised of 6-methoxy-2-naphthyllithium dissolved in tetrahydrofuran. To this product solution is added 16 grams of cuprous bromide, and the resultant slurry is stirred for one hour at about 20° C. to form a tetrahydrofuran solution of 6-methoxy-2-naphthylcopper (I).

(F) Preparation of (±)-2-(6-Methoxy-2-Naphthyl) Propionic Acid Using Bis(6-Methoxy-2-Naphthyl) Zinc, (6-Methoxy-2-Naphthyl)Zinc Halide or Mixtures Thereof as Reaction Intermediates In this embodiment any one or more of the zinc-containing (±)-2-(6-methoxy-2-naphthyl)propionic acid precursors formed as in (B) above is/are reacted with a lower alkyl 2-bromopropionate in an inert solvent until a lower alkyl 2-(6-methoxy-2-naphthyl)propionate is formed, and hydrolyzing the ester group of the lower alkyl 2-(6-methoxy-2-naphthyl)propionate to form 2-(6-methoxy-2-naphthyl)propionic acid. Preferably the recovered product is resolved in known manner to yield S(+)-2-(6-methoxy-2-naphthyl)propionic acid (naproxen). For further details concerning the synthesis of bis(6-methoxy-2-naphthyl)zinc, (6-methoxy-2-naphthyl)zinc halide or mixtures thereof pursuant to this invention, the reader is referred to (B) above, and the reference cited therein. Further details concerning the synthesis of (±)-2-(6-methoxy-2-naphthyl)propionic acid using bis(6-methoxy-2-naphthyl)zinc, (6-methoxy-2-naphthyl)zinc halide or mixtures thereof one should refer to U.S. Pat. No. 3,663,584 referred to above and incorporated herein. Pursuant to this invention, the bis(6-methoxy-2-naphthyl)zinc, (6-methoxy-2-naphthyl)zinc halide or mixture thereof used in such operations is ultimately formed from 2-bromo-6-methoxynaphthalene produced as described hereinabove. The following Example 73 which illustrates the practice of this invention is based in part on the procedure U.S. Pat. No. 3,663,584 (supra).

EXAMPLE 73

To the benzene solution of bis(6-methoxy-2-naphthyl) zinc formed in Example 61 above is added 9.96 grams of ethyl 2-bromopropionate in 5 mL of anhydrous benzene. The temperature of the reaction mixture is maintained at from 50° to 55° C. for 15 hours, under nitrogen, and then the reaction mixture is mixed with 175 mL of 1.5N hydrochloric acid solution, followed by 65 mL of methylene chloride. The mixture is filtered, and the organic phase is separated. The aqueous acid layer is extracted with two further 30 mL quantities of methylene chloride, and the methylene chloride extracts are combined, washed with 50 mL of water, and stripped of solvents under vacuum to yield ethyl 2-(6-methoxy-2-naphthyl)propionate. A solution of 6.0 grams of potassium hydroxide, 6 mL of water and 60 mL of methanol is added to the ethyl 2-(6-methoxy-2-naphthyl)propionate, and the mixture is heated at reflux for 45 minutes, cooled to ambient temperature, acidified and mixed with 60 mL of water. Methanol is removed by evaporation in vacuo, and the resultant solution is extracted with two 60 mL portions of methylene chloride. The combined methylene chloride extracts are evaporated to dryness to yield 2-(6-methoxy-2-naphthyl)propionic acid.

(G) Preparation of (±)-2-(6-Methoxy-2-Naphthyl) Propionic Acid Using Bis(6-Methoxy-2-Naphthyl) Cadmium, (6-Methoxy-2-Naphthyl)Cadmium Halide or Mixtures Thereof, as Reaction Intermediates In this embodiment any one or more of the cadmium-containing, (±)-2-(6-methoxy-2-naphthyl)propionic acid precursors formed as in (C) above is/are reacted with a lower alkyl 2-bromopropionate in an inert solvent until a lower alkyl 2-(6-methoxy-2-naphthyl)propionate is formed, and hydrolyzing the ester group of the lower alkyl 2-(6-methoxy-2-naphthyl)propionate to form 2-(6-methoxy-2-naphthyl)propionic acid. Preferably the recovered product is resolved in known manner to yield S(+)-2-(6-methoxy-2-naphthyl)propionic acid (naproxen). For further details concerning the synthesis of bis(6-methoxy-2-naphthyl) cadmium, (6-methoxy-2-naphthyl)cadmium halide or mixtures thereof pursuant to this invention, the reader is referred to (C) above, and the references cited therein. For further details concerning the synthesis of (±)-2-(6-methoxy-2-naphthyl)propionic acid using bis(6-methoxy-2-naphthyl)cadmium, (6-methoxy-2-naphthyl)cadmium halide or mixtures thereof one should refer to U.S. Pat. Nos. 3,658,858 and 3,694,476 both referred to above and incorporated herein. Pursuant to this invention, in all cases the bis(6-methoxy-2-naphthyl)cadmium, (6-methoxy-2-naphthyl)cadmium halide or mixture thereof used in such operations is ultimately formed from 2-bromo-6-methoxynaphthalene produced as described hereinabove. The following Example 74 which illustrates the practice of this invention is based in part on the procedures of U.S. Pat. No. 3,658,858 (supra).

EXAMPLE 74

A solution is formed by dissolving 24 grams of 2-bromo-6-methoxynaphthalene prepared as in Example 7 above in 300 mL of tetrahydrofuran. The resulting solution is slowly added to 2.5 grams of magnesium turnings in 100 mL of tetrahydrofuran at reflux temperature. After the addition is complete, 20 grams of cadmium chloride is added, and the resultant mixture is refluxed for 10 minutes to yield a solution of 6-methoxy-2-naphthylcadmium chloride in tetrahydrofuran. A solution of 18 grams of ethyl 2-bromopropionate in 20 mL of tetrahydrofuran is then added to the cooled reaction mixture. After 24 hours at 20° C., the product is hydrolyzed by adding 200 mL of 5 weight percent methanolic sodium hydroxide followed by heating to reflux for 1 hour. The reaction mixture is then diluted with excess 1N sulfuric acid and extracted with ether. The ether phase is separated, evaporated to dryness and the residue is recrystallized from acetone-hexane to yield 2-(6-methoxy-2-naphthyl)propionic acid.

(H) Preparation of (±)-2-(6-Methoxy-2-Naphthyl) Propionic Acid Using 6-Methoxy-2-NaphthylCopper(I), as a Reaction Intermediate In this embodiment 6-methoxy-2-naphthylcopper(I) formed as in (E) above is reacted with a lower alkyl 2-bromopropionate in a suitable solvent until a lower alkyl 2-(6-methoxy-2-naphthyl)propionate is formed, and hydrolyzing the ester group of the lower alkyl 2-(6-methoxy-2-naphthyl)propionate to form 2-(6-methoxy-2-naphthyl) propionic acid. Preferably, the recovered product is resolved in known manner to yield S(+)-2-(6-methoxy-2-naphthyl) propionic acid (naproxen). For further details concerning the synthesis of 6-methoxy-2-naphthylcopper(I) pursuant to this invention, the reader is referred to (E) above, and the references cited therein. For further details concerning the synthesis of (±)-2-(6-methoxy-2-naphthyl)propionic acid using 6-methoxy-2-naphthylcopper(I), one should refer to U.S. Pat. No. 3,658,863 referred to above and incorporated herein. Pursuant to this invention, in all cases the 6-methoxy-2-naphthylcopper(I) used in such operations is ultimately formed from 2-bromo-6-methoxynaphthalene produced as described hereinabove. The following Example 75 which illustrates the practice of this invention is based in part on the procedures of U.S. Pat. No. 3,658,863 (supra).

EXAMPLE 75

A solution is formed from 23 grams of 2-bromo-6-methoxynaphthalene produced as in Example 7 above and 100 mL of tetrahydrofuran, and is slowly added to 1.4 g of lithium metal in 100 mL of tetrahydrofuran. When most of the lithium has reacted, 16 grams of cuprous bromide is added, and the suspension is stirred for 1 hour at about 20° C. to form 6-methoxy-2-naphthylcopper(I). The tetrahydrofuran is then removed in vacuo while maintaining the solution temperature at less than 30° C. to yield 6-methoxy-2-naphthyl copper(I). A solution of 18 grams of ethyl 2-bromopropionate in 50 mL of dimethylformamide is added to the residue, and the mixture is heated to 40° C. for 24 hours. The solvent is then removed in vacuo, and the residue is hydrolyzed by heating under reflux for 1 hour with a solution of 10 grams of sodium hydroxide in 250 mL of methanol. The alkaline solution is filtered, and the filtrate acidified with 2N hydrochloric acid to yield 2-(6-methoxy-2-naphthyl)propionic acid which precipitates from the solution. The precipitate is filtered, and the filtered solids are dried and recrystallized from acetone-hexane.

(I) Preparation of (±)-2-(6-Methoxy-2-Naphthyl) Propionic Acid Using Grignard Reagent of 2-Bromo-6-Methoxynaphthalene and a Salt of 2-Bromopropionic Acid as Reaction Intermediates In accordance with this embodiment, (±)-2-(6-methoxy-2-naphthyl)propionic acid is formed by reaction of a light metal salt of 2-bromopropionic acid with a Grignard reagent formed pursuant to this invention from 2-bromo-6-methoxynaphthalene produced as described hereinabove, followed by acidification of the product formed in this reaction. The light metal salts include the lithium, sodium, magnesium and calcium salts of 2-bromopropionic acid. The Grignard reagents are formed pursuant to this invention as in (A) above. Detailed procedures which can be employed in effecting this process are set forth in U.S. Pat. No. 3,959,364 referred to above and incorporated herein by reference. Preferably, the reaction involving the Grignard reagent is performed in an ethereal reaction medium such as tetrahydrofuran, and typically, but not necessarily, at one or more temperatures in the range of 0° to about 80° C. The acidification is typically conducted using an aqueous mineral acid such as sulfuric or hydrochloric acid. The following Examples 76–80 of the practice of this invention are based in part on procedures described in U.S. Pat. No. 3,959,364 (supra).

EXAMPLE 76

A solution of Grignard reagent is formed in dry tetrahydrofuran (15 mL) under a nitrogen atmosphere from 0.25 gram of magnesium turnings and 2.45 grams (0.01 mol) of 2-bromo-6-methoxynaphthalene produced as in Example 7 above. When the portionwise addition of the reactants is completed, the mixture is stirred and boiled under reflux for 30 minutes. The mixture is then cooled and a suspension of sodium 2-bromopropionate (1.75 g; 0.01 mol) in dry tetrahydrofuran (20 mL) is slowly added. After boiling the mixture under reflux with stirring for one hour, the mixture is then cooled in an ice-bath, and water (15 mL) is added, followed by sulfuric acid (20%; 5 mL). The mixture is stirred for 10–15 minutes, and extracted with ether. The extract is washed with water and then extracted with aqueous potassium carbonate (1N). This extract is washed with ether and then added to a mixture of concentrated hydrochloric acid (10 mL) and water (20 mL). The mixture is cooled overnight and the precipitate is filtered, washed with water and dried in vacuo to give 2-(6-methoxy-2-naphthyl) propionic acid.

The sodium 2-bromopropionate used above is prepared by adding methanolic sodium methoxide to a stirred, cooled solution of an equivalent amount of 2-bromopropionic acid in anhydrous methanol (10 molar). The mixture is stirred for a further 15 minutes at room temperature and methanol evaporated under reduced pressure. The residue is finely ground and dried at 55°–60° C. in vacuo.

EXAMPLE 77

Example 76 is repeated except that before addition of the sodium 2-bromopropionate, the solution of the Grignard reagent is cooled in an ice bath to 0° to 5° C., and after the addition the mixture is maintained at this temperature and stirred for one hour instead of being boiled under reflux.

EXAMPLE 78

Example 76 is repeated except that the sodium 2-bromopropionate used is prepared by adding anhydrous sodium carbonate, portionwise, to a stirred, cooled solution of an equivalent amount of 2-bromopropionic acid in anhydrous methanol (5 molar). This solution is then stirred for a further 45 minutes at room temperature during which time a further portion of methanol equal to half the original volume is added to prevent crystallization of the salt. The methanol is then evaporated under reduced pressure, and the residue is finely ground and dried at 55°–60° C. in vacuo.

EXAMPLE 79

Example 76 is repeated except that the sodium 2-bromopropionate used is prepared by adding freshly prepared sodium tert-butoxide, portionwise, under nitrogen, to a stirred, cooled solution of an equivalent amount of 2-bromopropionic acid in anhydrous methanol (2.5 molar). This solution is stirred for a farther 10 minutes at room temperature and methanol is evaporated under reduced pressure. The residue is finely ground and dried at 55°–60° C. in vacuo.

EXAMPLE 80

Example 76 is repeated except that the reactions are carried out at 0° to 10° C.

(J) Preparation of (±)-2-(6-Methoxy-2-Naphthyl) Propionic Acid Using Grignard Reagent of 2-Bromo-6-Methoxynaphthalene and a Mixed Magnesium Halide Complex of 2-Bromopropionic Acid as Reaction Intermediates In accordance with this embodiment of the invention, (±)-2-(6-methoxy-2-naphthyl)propionic acid is formed by (i) reaction of a mixed magnesium halide complex of 2-bromopropionic acid with a Grignard reagent formed pursuant to this invention from 2-bromo-6-methoxynaphthalene produced as described hereinabove, followed by (ii) acidification of the product formed in reaction (i). The mixed magnesium halide complex of 2-bromopropionic acid can be represented by the formula $CH_3CH(Br)COOMgX$ wherein X is chloride or bromide, and the complex may be prepared by treatment of the free 2-bromopropionic acid with a suitable Grignard reagent, which preferably is a $C_{1-12}$ alkyl Grignard reagent or a $C_{6-9}$ aryl Grignard reagent. Methyl magnesium chloride and methyl magnesium bromide are particularly preferred because of their availability and because during the reaction with the Grignard reagent formed pursuant to this invention (i.e., from 2-bromo-6-methoxynaphthalene produced as described hereinabove), the methyl Grignard results in release of methane which escapes from the reaction mixture as a gas, and does not interfere with the reaction or subsequent product workup. The Grignard reagents formed from 2-bromo-6-methoxynaphthalene are formed pursuant to this invention as in (A) above. Detailed procedures which can be employed in preparing the mixed magnesium halide complex of 2-bromopropionic acid, and in effecting the reaction between the mixed magnesium halide complex of 2-bromopropionic acid and the Grignard reagent formed from 2-bromo-6-methoxynaphthalene are set forth in U.S. Pat. No. 4,144,397 referred to above and incorporated herein in full by reference, and in accordance with this invention such procedures are modified by use of Grignard reagent formed pursuant to this invention from 2-bromo-6- methoxynaphthalene made as described hereinabove. Preferably, the reaction involving the Grignard reagent is performed in an ethereal reaction medium such as tetrahydrofuran, and typically, but not necessarily, at one or more temperatures in the range of 0° to about 100° C., and preferably between about 10° and about 60° C. Preferably, the reactants are employed in approximately equimolar proportions. The acidification is typically conducted by quenching the reaction mixture with acid such as aqueous mineral acid (e.g., sulfuric or hydrochloric acid). The following Examples 81–90 of the practice of this invention are based in part on procedures described in U.S. Pat. No. 4,144,397 (supra).

EXAMPLE 81

Preparation of Mixed Magnesium Halide Complex of 2-Bromopropionic Acid 15.3 Grams (0.1 molee) of 2-bromopropionic acid and 40 mL of toluene are cooled to 10° C. and a solution of 50 mL of 2M methylmagnesium bromide in tetrahydrofuran/toluene (1:1) is then added slowly, maintaining the temperature at 10°–20° C. during the addition time of 15–20 minutes. The reaction mixture is then stirred at 5° C. for an additional 20 minutes to afford a 1.1M solution of the complex.

Preparation of (±)-2-(6-Methoxy-2-Naphthyl) Propionic Acid

The above 1.1M solution of the complex is added slowly to the 1.0M Grignard solution prepared as in Example 59 above. The temperature is maintained at 15°–20° C. during the addition time of 10–15 minutes. The reaction mixture is allowed to warm up to room temperature and then stirred for two hours. The reaction mixture is then cooled in an ice bath and a solution of 20 mL of 12N hydrochloric acid and 150 mL of water are added. After stirring for 5 minutes, the two-phase system is filtered and the filter cake is washed with 55 mL of toluene and 50 mL of water. The organic phase is extracted with 10% potassium hydroxide solution (2×150 mL) and the combined basic extracts are washed with toluene (30 mL) and neutralized with 12N hydrochloric acid to pH 1. The white solid 2-(6-methoxy-2-naphthyl) propionic acid is filtered under vacuum and dried at 55° C. in vacuo.

EXAMPLE 82

The procedure of Example 81 is repeated except that the 1.1M solution of the mixed magnesium halide complex is prepared utilizing tetrahydrofuran as the sole solvent.

EXAMPLES 83 AND 84

The respective procedures of Examples 81 and 82 are repeated except that in preparing the 1.1M solutions of the mixed magnesium halide complex, the methylmagnesium bromide solution is replaced in each case by an equal amount of an analogous methylmagnesium chloride solution.

EXAMPLES 85–88

The respective procedures of Examples 81–84 are repeated except that in each case, after the filtration in the (±)-2-(6-methoxy-2-naphthyl)propionic acid synthesis, the organic phase is extracted with 10% potassium hydroxide solution (2×150 mL) which is washed with toluene (30 mL) and filtered. Methanol (15 mL) and toluene (12 mL) are added, then sufficient 12N hydrochloric acid to bring the pH to between 4 and 5. The resulting slurry is then heated to reflux for 1 hour, cooled and filtered. The precipitate is washed with water (20 mL), toluene (2×3 mL), and hexane (2×3 mL) and dried at 55° C. in vacuo.

EXAMPLE 89

Sixty-seven milliliters of a 1.5M solution of a mixed magnesium chloride complex of alpha-bromopropionic acid in tetrahydrofuran (prepared utilizing 3M methylmagnesium chloride) is slowly added to a cooled (10° C.) solution of 2-(6-methoxynaphthyl)magnesium bromide (1.5M) in tetrahydrofuran (67 mL) (prepared by utilizing 2-bromo-6-methoxynaphthalene formed as in Example 7 hereof) at a rate such that the temperature is held at 55° C. or below. The resulting slurry is stirred at 50° C. for one hour and then heated to reflux, allowing 30–40% of the tetrahydrofuran to distill off. The reaction mixture is cooled to 50° C., 30 mL of toluene is added, and the reaction mixture is quenched with aqueous hydrochloric acid and worked up using the workup procedure described in Examples 85–88 hereof to afford 2-(6-methoxy-2-naphthyl)propionic acid.

EXAMPLE 90

(a) Preparation of Grignard Reagent

2-Bromo-6-methoxynaphthalene (25 mmol) formed as in Example 7 hereof is dissolved in 18 mL of tetrahydrofuran. This solution is then added to an excess of magnesium metal (3 grams; 0.012 mol) and tetrahydrofuran (7 mL) under a nitrogen atmosphere. The temperature is maintained at 50°–60° C. with cooling during the addition period of 10–15 minutes. The reaction mixture is then transferred away from the excess magnesium to a clean dry vessel under nitrogen and stored at 10° C. to afford a 1.0 molar Grignard reagent, viz., 2-(6-methoxynaphthyl)magnesium bromide.

(b) Preparation of Mixed Magnesium Halide Complex of 2-Bromopropionic Acid

2-Bromopropionic acid (3.8 grams; 25 mmol) is dissolved in tetrahydrofuran (8 mL) and the solution is cooled to −10° C. To this solution is added methyl magnesium chloride in tetrahydrofuran (8 mL, 3M) over a 15-minute period while maintaining the temperature at −10° to 0° C. This affords a 1.1 molar solution of the complex which is stored at 0° C. or below until use.

(c) Preparation of (±)-2-(6-Methoxy-2-Naphthyl) Propionic Acid

The 1.0 molar Grignard reagent produced in part (a) hereof is cooled to 10° C. and the solution of the magnesium chloride complex in tetrahydrofuran produced in part (b) hereof is added over a five-minute period while maintaining the temperature at 10° to 55° C. The reaction mixture is then stirred at 25°–30° C. for two hours. The reaction mixture is then cooled to 10° C. and a solution of hydrochloric acid (10 mL, 12N) and water (50 mL) is added. Toluene (50 mL) is then added and the aqueous phase is separated and discarded. The organic phase is extracted with 10% potassium hydroxide (2×50 mL). The basic extracts are combined and neutralized with hydrochloric acid to give a precipitate of 2-(6-methoxy-2-naphthyl)propionic acid which is filtered and dried at 50° C.

(K) Preparation of 6-Methoxy-2-Vinylnaphthalene, a Precursor of (±)-2-(6-Methoxy-2-Naphthyl) Propionic Acid This embodiment involves the reaction of ethylene with 2-bromo-6-methoxynaphthalene to form 6-methoxy-2- vinylnaphthalene. where the 2-bromo-6-methoxynaphthalene used is prepared as described hereinabove. The reaction for producing 6-methoxy-2-vinylnaphthalene is catalyzed by a palladium catalyst used in conjunction with a suitable ligand, which preferably is a tri-substituted phosphine where two of the substituents are aryl groups and the third substituent is a cycloaliphatic group. Such catalytic systems are described for example in U.S. Pat. No. 5,536,870 (Jul. 16, 1996) to T. C. Wu, the entire disclosure of which is incorporated herein by reference. Preferred palladium compounds are the Pd(II) salts such as palladium (II) chloride, palladium (II) acetate, and analogous Pd(II) salts. Preferred phosphine ligands are those depicted and described in the foregoing patent to T. C. Wu (e.g., at Column 4, lines 40–57 thereof). Neomenthyldiphenylphosphine is a particularly preferred ligand for use in this process. The reaction is typically, but not necessarily, conducted at one or more temperatures in the range of about 30° to about 200° C., and preferably at one or more temperatures in the range of about 60° to about 150° C. Pressures used are typically, but not necessarily, in the range of about 50 to about 3000 psig and preferably are in the range of about 400 to about 1000 psig. The reaction is best conducted in a suitable polar liquid solvent/diluent, such as, for example, acetonitrile, tetrahydrofuran, diglyme, 1,4-dioxane, tetrahydropyran, N,N-dimethylformamide, N,N-dimethylacetamide, diethylketone, and analogous compounds. Non-polar solvent/diluents such as aromatic hydrocarbons can be used but are less preferred. Mixtures of two or more solvent/diluents can be used as the liquid reaction medium, if desired. Liquid nitriles such as acetonitrile and/or ketones such as diethyl ketone are particularly preferred solvent/diluents for use in the process. Typically ethylene is used in excess relative to the 2-bromo-6-methoxynaphthalene, and the amount of Pd(II) salt used is typically, but not necessarily, an amount that provides a molar ratio of palladium to 2-bromo-6-methoxynaphthalene in the range of about 0.00001:1 up to about 0.01:1, e.g., 0.0005:1. The molar ratio of ligand to Pd(II) salt used typically, but not necessarily, corresponds to amounts that provide a ratio of phosphorus to palladium in the range of about 2:1 up to about 20:1, e.g., about 6:1. Hydrogen bromide co-product of the reaction can be stripped from the reaction mixture as formed or it can be reacted in situ with a suitable base such as a tertiary amine to form the amine hydrobromide salt. The use of amine such as triethylamine is highly desirable as the inclusion of an amine in the reaction mixture ensures high conversions. Thus, an amine is typically used in small molar excess over the amount of 2-bromo-6-methoxynaphthalene charged, e.g., about 1.05–1.2 mole of monoamine per mole of 2-bromo-6-methoxynaphthalene. If a polyamine is used, this excess is based on equivalents of amine per mole of 2-bromo-6-methoxynaphthalene. For example, 0.5 mole of a diamine is one equivalent, and thus, if a diamine such as N,N,N',N'-tetramethylethylene diamine is used, the molar ratio is typically about 0.525–0.6 mole thereof per mole of 2-bromo-6-methoxynaphthalene.

One preferred general procedure for producing 6-methoxy-2-vinylnaphthalene in accordance with this invention is as follows:

(a) Produce 2-bromo-6-methoxynaphthalene using the three-stage procedure set forth above under the heading "Three-Stage Process for Producing 2-Bromo-6-Methoxynaphthalene".

(b) Use 2-bromo-6-methoxynaphthalene produced as in (a) immediately above in the process set forth in (c) immediately below.

(c) Charge 2-bromo-6-methoxynaphthalene (BMN) of (b) immediately above, palladium(II) chloride (PDC), triethylamine (TEA) and acetonitrile solvent to a stainless steel reactor at a 2000:1 BMN:PDC weight ratio, and a mole ratio of TEA:BMN of 1.05–1.2:1. Add neomenthyldiphenylphosphine (NMDP) to the mixture at a 6:1 NMDP:PDC ratio to form a soluble palladium-containing catalytic mixture or species in the reaction mixture. Conduct the reaction at 95° C. with agitation and at 500–550 psig ethylene pressure for a reaction period of about three hours. Add diethyl ketone to the reaction mixture, and wash the mixture with aqueous caustic. Remove triethylamine and acetonitrile by staged distillation leaving a mixture of 6-methoxy-2-vinylnaphthalene (MVN) and diethyl ketone in the bottoms. The MVN is recovered by distillation at 100 mm Hg and a bottoms temperature of 40°–50° C.

The following Example 91 further illustrates the practice of this embodiment of the invention.

EXAMPLE 91

To a 5-gallon stainless steel electrically heated reactor is added 1,485 grams (6.26 mol) of 2-bromo-6-methoxynaphthalene (BMN) (produced as in Example 7 hereof, added as a dry powder through a 2" opening in the reactor head), 672 grams (6.64 mol) of triethylamine, 0.56 grams of $PdCl_2$ (3.2 mmol) and 6.2 grams of NMDP (19 mmol). The reactor is purged three times with nitrogen (50 psig) and then three times with ethylene (50 psig). The reactor is charged with ethylene (about 300 psig) and then warmed at 95° C. Ethylene pressure in the reactor is raised to about 550 psig after reaching reaction temperature. When the reaction is completed, the reaction mixture is cooled to below 50° C. and the ethylene is vented. Diethyl ketone (3,835 g) is added to the reaction mixture. Aqueous sodium hydroxide (24.8 wt %) is then added to the reaction mixture to neutralize the triethylamine hydrobromide salt formed during the reaction. The aqueous phase is removed, as well as possible at this point, from the reactor. The reaction mixture is filtered using a medium porosity 3-liter sintered glass funnel and any further aqueous phase that separates is removed. The volatile organics (acetonitrile, diethyl ketone, triethylamine) are removed at reduced pressure (1 mm Hg, 45° C.) to give 6-methoxy-2-vinylnaphthalene as a yellow solid.

When preparing 6-methoxy-2-vinylnaphthalene from 2-bromo-6-methoxynaphthalene formed as described above, it is preferable to conduct the reaction using the following components in forming the reaction mixture:

A) 2-bromo-6-methoxynaphthalene;

B) ethylene

C) a polar liquid reaction medium formed from (i) at least one liquid organic solvent/diluent, and (ii) at least one liquid secondary or tertiary amine as a hydrogen halide acceptor in an amount of at least one equivalent per mole of the 2-bromo-6-methoxynaphthalene;

D) a catalytically effective amount of a catalyst system formed from (i) palladium or Pd(0) compound, and/or at least one salt of palladium in which the palladium has a valence of 1 or 2, and (ii) a tertiary phosphine ligand of the formula

where $R^4$, $R^5$, and $R^6$ are the same or different and are selected from alkyl, aryl, substituted aryl, heteroaryl, substituted heteroaryl, aralkyl, substituted aralkyl, cycloalkyl, and substituted cycloalkyl, at least one of $R^4$, $R^5$, and $R^6$ being aryl; and E) a reaction accelerating amount of water in the range of about 0.5 to about 5 weight percent of the total weight of A), B), C), D), and E).

The liquid organic solvent/diluent, C) above, is preferably diethyl ketone, and the amine of C) is preferably triethylamine. The catalyst of D) above is preferably formed by including in the reaction mixture before, during and/or after the formation of the rest of the initial reaction mixture catalytically effective amounts of (i) at least one salt of palladium in which the palladium has a valence of 1 or 2, most preferably $PdCl_2$, and (ii) neomenthyldiphenylphosphine. The reaction accelerating amount of water is most preferably in the range of about 1.5 to about 3.5 weight percent of the total weight of A), B), C), D), and E).

Examples 98 and 99 hereinafter illustrate, among other things, how this process can be utilized very effectively on a large (1000 gallon) scale.

(L) Preparation of (±)-2-(6-Methoxy-2-Naphthyl) Propionic Acid from 6-Methoxy-2-Vinylnaphthalene, a Precursor of (±)-2-(6-Methoxy-2-Naphthyl)Propionic Acid In this embodiment of the invention 6-methoxy-2-vinylnaphthalene formed as in (K) above is subjected to hydrocarboxylation using carbon monoxide and water or hydrocarbalkoxylation using carbon monoxide and an alcohol. These operations can be conducted using procedures and conditions such as are disclosed in U.S. Pat. No. 5,536,870 (Jul. 16, 1996) to T. C. Wu. A suitable co-solvent such as tetrahydrofuran is also preferably used. The reaction is catalyzed by a catalyst formed from palladium(0) and/or at least one of the compounds or salts of palladium having a valence of 0, 1 or 2, preferably a Pd(II) salt, and a suitable ligand such as a tri-substituted phosphine. Thus, the palladium catalysts and the phosphine ligands referred to in (K) above are suitable for use in the hydrocarboxylation reaction. Other components can be charged to the reaction system to enhance the catalytic process by mechanisms which have not been fully elucidated. Such components are a water-soluble copper(II) salt such as copper(II) chloride, and hydrochloric acid plus water, e.g., dilute hydrochloric acid, such as 10 wt % aqueous HCl. The amount of Pd(II) salt used is typically, but not necessarily, an amount that provides a molar ratio of 2-bromo-6-methoxynaphthalene to palladium in the range of about 500:1 up to about 50,000:1, and preferably in the range of about 1500:1 to about 3000:1. The molar ratio of ligand to Pd(II) salt used typically, but not necessarily, corresponds to amounts that provide a ratio of phosphorus to palladium in the range of about 2:1 up to about 20:1, e.g., about 6:1. The molar ratio of Cu(II) salt to Pd(II) salt used typically, but not necessarily, corresponds to amounts that provide a ratio of copper to palladium in the range of up to about 10:1, and preferably in the range of about 1:1 up to about 3:1. As indicated above, it is possible to omit the copper entirely, if desired. Dilute aqueous Hcl not only enhances the catalyst but supplies water for the reaction. Amine such as triethyl amine, when present at levels of 2% in the reaction mixture, inhibits the hydrocarboxylation reaction. Since it is desirable to use amine in the vinylation reaction, it is, therefore, important to ensure that amine carryover, if any, from the vinylation reaction is kept to a sufficiently low level as not to materially inhibit the hydrocarboxylation reaction. The hydrocarboxylation reaction is typically, but not necessarily, conducted at about 0 to about 3000 psig carbon monoxide pressure and one or more temperatures in the range of about 25° to about 200° C. The reaction is exothermic and thus adequate cooling means should be available when performing this reaction. Reaction periods typically fall in the range of about 1 to about 10 hours. Further details concerning conditions, and catalyst and co-solvent materials, that can be used in this process are set forth in U.S. Pat. No. 5,536,870 referred to above and incorporated herein in full by reference.

One preferred general procedure for producing (±)-2-(6-methoxy-2-naphthyl)propionic acid from 6-methoxy-2-vinylnaphthalene in accordance with this invention is as follows:

Using 6-methoxy-2-vinylnaphthalene formed per (K) above, such as in (c) of the general procedure thereof, charge the following ingredients to a suitable reactor such as a 2-L Hastalloy C Parr reactor: 6-methoxy-2-vinylnaphthalene (MVN), $PdCl_2$, $CuCl_2$, tetrahydrofuran, aqueous HCl, and neomenthyldiphenylphosphine. Seal the reactor and purge several times with carbon monoxide. Then fill the reactor with carbon monoxide and apply heat to the reactor contents. Keep the temperature at about 90° C. while stirring the reaction mixture until completion of the reaction. Recover the (±)-2-(6-methoxy-2-naphthyl)propionic acid from the reaction mixture as sodium (±)-2-(6-methoxy-2-naphthyl) propionate by adding water, toluene and excess aqueous caustic (e.g., 5 to 20% excess as a 20–25% solution) to the reaction mixture, stirring the resultant mixture, and then separating the organic layer from the aqueous phase containing sodium (±)-2-(6-methoxy-2-naphthyl)propionate. Additional workup procedures can be employed to increase the yield and purity of recovered sodium (±)-2-(6-methoxy-2-naphthyl)propionate. This typically involves washing the aqueous phase several times with toluene or like solvent to extract neutral organics remaining therein. Acidification of the sodium (±)-2-(6-methoxy-2-naphthyl)propionate yields (±)-2-(6-methoxy-2-naphthyl)propionic acid. One preferred way of carrying out the acidification involves adding toluene to the toluene-washed aqueous phase, warming to about 80° C., and acidifying with aqueous sulfuric acid. The (±)-2-(6-methoxy-2-naphthyl)propionic acid is isolated by allowing the hot toluene solution to cool to room temperature to crystallize the dissolved (±)-2-(6-methoxy-2-naphthyl) propionic acid. The (±)-2-(6-methoxy-2-naphthyl)propionic acid crystals are collected, rinsed with toluene, rinsed with heptane or pentane to facilitate drying, and brought to constant weight in a vacuum oven operated for example at 52° C. and 2 mm Hg.

Additional examples of the practice of this invention are given below.

EXAMPLE 92

Preparation of 6-Methoxy-2-Vinylnaphthalene

A 20-gallon jacketed stainless steel reactor equipped with a mechanical agitator is charged with 19.45 kg of acetonitrile (ACN) and 12.45 kg of 2-bromo-6-methoxynaphthalene (BMN) formed as described in Example 7 hereof, and 4.8 g of $PdCl_2$. The reactor is pressured and vented three times with 50 psig nitrogen. The reactor is then charged with 5.3 kg of ACN and 5.64 kg of triethylamine (TEA). The agitator is set at 158 rpm and the reactor is pressured and vented three times with 80 psig nitrogen. The reactor is then purged for ten minutes with nitrogen. Next a mixture of 48.6 g of neomenthyldiphenylphosphine (NMDP) dissolved in 0.35 kg of TEA is charged to the reactor. The agitator is set to 412 rpm and the reactor is heated with steam on the jacket. The reaction temperature is initially in the range of 91°–109° C., while the pressure varies from 412°–519 psig. The reaction produces a heat kick, and after 30 minutes the temperature rises to 109° C. with 26° C. cooling water on the jacket. The total reaction time is 1.75 hours with a BMN conversion of 100%. The reactor is cooled, vented, and the reactor contents are transferred to a 30-gallon glass lined reactor for workup.

Workup of 6-Methoxy-2- Vinylnaphthalene

The crude 6-methoxy-2-vinylnaphthalene (MVN) solution in the 30-gallon reactor is stripped at 330 mm Hg to remove the ACN. The total strip time is 6.33 hours with a maximum bottoms temperature of about 91° C. The final overhead temperature is about 68° C. Zero reflux is used for the first 35 minutes of operation. The reflux ratio is then set to five, and 34.95 kg of diethyl ketone (DEK) is added to the reactor contents. The reflux ratio remains at five for the duration of the strip.

After charging 9.25 kg of 25% NaOH to the stripped reaction product in the 30-gallon reactor, the resultant mixture is agitated for 30 minutes. Then the agitator is shut off and the aqueous phase is allowed to settle for 1.75 hours. The mixture is phase cut at 57° C., and the aqueous phase is collected and discarded. The organic phase and rag layer in the reactor are stripped to remove TEA. The strip pressure is 330 mm Hg. The total strip time is 4.9 hours. The column is started up under total reflux for the first 30 minutes of operation. The reflux ratio is then lowered to three for 3.5 hours. The reflux ratio is reduced to two for the remainder of the strip. The final overhead temperature is about 79° C. and the final bottoms temperature is about 86° C.

To the cooled-down stripped mixture in the 30-gallon reactor is added 8 kg of tetrahydrofuran (THF). The resultant MVN solution is filtered through a 10 micron bag filter and a 1 micron cartridge filter.

Hydrocarboxylation of 6-Methoxy-2- Vinylnaphthalene

A 20-gallon Hastalloy reactor is purged three times with 80 psig nitrogen, and then 3.8 g of PdCl$_2$ and 8.8 g of CuCl$_2$ are charged to the reactor, followed by the MVN solution. The reactor is purged three more times with 80 psig nitrogen and the agitator is set to 118 rpm. After charging 3.6 kg of THF and 3.55 kg of 10% Hcl to the reactor, the reactor is again purged three times with 80 psig nitrogen and then nitrogen is bubbled through a dip leg for ten minutes. Next, a mixture of 42.2 g of NMDP and 0.35 kg of THF is charged to the reactor and the agitator is set at 402 rpm. The reactor is pressured and vented three times with 50 psig CO, and then heated to reaction temperature and pressured with CO. The reaction temperature is in the range of 70° to 78° C., while the pressure varies from 247 to 450 psig. After a total reaction time of 8.5 hours the reactor is cooled and vented, and the contents transferred to a 30-gallon glass-lined reactor for workup.

Product Workup

The hydrocarboxylation mixture is neutralized with 2.05 kg of 25% NaOH. THF is stripped at atmospheric pressure from the workup reactor contents over 2.5 hours. Water (30.7 kg) is charged 1.4 hours into the strip. The final overhead temperature is about 97° C. and the final bottoms temperature is about 108° C. To the stripped reactor contents is added 7 kg of 25% NaOH, and the mixture is agitated for 30 minutes at 50°–60° C. After a 35-minute settling time, the aqueous and organic phases are separated from each other. The aqueous phase is charged back to the workup reactor along with 10 kg of toluene. This mixture is agitated for 15 minutes and allowed to settle for 30 minutes at 55° C. The phases are again separated. The aqueous phase is charged back to the workup reactor along with 10 kg of toluene, the mixture is stirred for 15 minutes and then allowed to settle. The mixture is then heated to 65° C. and the phases are separated from each other. The aqueous phase is again charged back to the reactor along with 10 kg of toluene. The mixture is stirred for 15 minutes and allowed to settle for 30 minutes at 70° C., and a final phase cut is made. The separated aqueous phase is a clear amber aqueous solution of sodium (±)-2-(6-methoxy-2-naphthyl)propionate solution.

EXAMPLE 93

The procedure of Example 92 is repeated substantially as described with the following principal changes:

The initial charge to the first reactor is 21.4 kg of diethyl ketone (DEK), 12.4 kg of BMN made as in Example 7 hereof, and 4.6 g of PdCl$_2$. The second charge is 3.2 kg of DEK and 6.34 kg of TEA. The 10-minute nitrogen purge after the addition of the TEA addition is eliminated. The NMDP charge (50.9 kg) is added as a solution in 0.27 kg of DEK. The pressurizing with ethylene is started to 100 psig before beginning the heat up of the reactants. This vinylation reaction is conducted at 92°–98° C. and 393–429 psig.

The MVN workup involves addition of 10.15 kg of DEK, heating to 75° C., followed by the caustic wash, a phase cut, a water wash, another phase cut, and the TEA strip with a final overhead temperature of about 79° C. and a maximum bottoms temperature of about 97° C.

The hydrocarboxylation solvent is a mixture of residual DEK and 8.2 kg of added THF. The other components charged are 3.5 g of PdCl$_2$, 7.9 g of CuCl$_2$, 3.25 kg of 10% HCl, 37.9 g of NMDP in 160 g of DEK. The hydrocarboxylation reaction is performed for 8.7 hours, with temperatures in the range of 74° to 84° C. and pressures in the range of 321 to 476 psig.

The crude (±)-2-(6-methoxy-2-naphthyl)propionic acid is stripped of THF, converted to sodium (±)-2-(6-methoxy-2-naphthyl)propionate and washed three times with 5 kg of toluene to yield an aqueous solution of sodium (±)-2-(6-methoxy-2-naphthyl)propionate.

EXAMPLE 94

Preparation of 6-Methoxy-2- Vinylnaphthalene

A 20-gallon jacketed stainless steel reactor equipped with a mechanical agitator is charged with 12.8 kg of ACN, 12.45 kg of DEK and 12.4 kg of 2-bromo-6-methoxynaphthalene (BMN) formed as described in Example 7 hereof, 4.6 g of PdCl$_2$, and 50.9 g of NMDP. The reactor is pressured and vented three times with 50 psig nitrogen. The reactor is then charged with 6.27 kg of TEA. The agitator is set at 158 rpm and the reactor is pressured and vented with 50 psig nitrogen. The agitator is set to 416 rpm, the reactor is pressured to 100 psig with ethylene and heated with tempered water on the jacket. The reaction temperature ranges from 87° to 98° C., while the pressure varies from 394 to 458 psig. The total reaction time is 3.5 hours with a BMN conversion of 99.6% in two hours. The reactor is cooled, vented, and the reactor contents at 60° C. are transferred for workup, to a 30-gallon glass lined reactor equipped with a 6-inch column. The 20-gallon reactor is then charged with 12.5 kg of DEK, which is then heated to 60° C. and transferred to the 30-gallon reactor.

Workup of 6-Methoxy-2-Vinylnaphthalene

The crude 6-methoxy-2-vinylnaphthalene (MVN) solution in the 30-gallon reactor is stripped at 150 mm Hg to remove the ACN. The total strip time is 4 hours with a maximum bottoms temperature of about 73° C. The final overhead temperature is about 59° C. Reflux ratios used are 5:1 for 1.9 hours, 3:1 for 1.6 hours, and 4:1 for 1.5 hours.

After charging 9.3 kg of 25% NaOH to the stripped reaction product in the 30-gallon reactor, the resultant mixture is agitated for 15 minutes at 35° C. Then the agitator is shut off and the aqueous phase is allowed to settle for 30 minutes. The mixture is phase cut and the organic phase is washed in the reactor with 1.2 kg of water with stirring for 15 minutes. After allowing a settling period of 30 minutes, another phase cut is made. A TEA strip of the organic phase is conducted at 150 mm Hg. The total strip time is 5.25 hours. The highest overhead temperature is about 59° C. and the maximum bottoms temperature is about 91° C. The reflux ratios were 50:1 at start up, and when the column stabilized, the reflux ratio was reduced to 5:1 for 2.25 hours and 7:1 for the final 2.5 hours of the strip. The reaction product is then diluted by addition to the reactor of 12.05 kg of THF and 2.05 kg of of DEK. The resulting solution is then filtered through a ten-micron bag filter and a one-micron cartridge filter.

Hydrocarboxylation of 6-Methoxy-2-Vinylnaphthalene

The filtered MVN solution is charged to a 20-gallon Hastalloy reactor followed by an additional 4.65 kg of DEK. Then 4.6 g of $PdCl_2$ and 10.5 g of $CuCl_2$ are charged to the reactor. The reactor is purged three times with 50 psig nitrogen, and 4.2 kg of 10% Hcl is charged. The reactor is pressured to 80 psig with nitrogen and vented. A solution of 50.9 g of NMDP in 255 g of DEK is charged to the reactor and the reactor is pressured and vented twice with 50 psig nitrogen with the agitator running only when pressurising. The agitator speed is set at 399 rpm and the reactor is pressured and vented three times with 50 psig CO, again agitating only during pressurization. The reactor is then pressured to 280 psig with CO and heated to 75° C. The reaction temperature is kept in the range of about 73° to about 77° C., while the pressure varies from 339 to 350 psig. After a total reaction time of 6 hours the reactor is cooled and vented, and the contents transferred to a 30-gallon glass-lined reactor for workup.

Product Workup

The hydrocarboxylation mixture is neutralized with 2.15 kg of 25% NaOH. THF is stripped from the hydrocarboxylation mixture at atmospheric pressure over 1.2 hours. The final bottoms temperature is 100° C. and the final overhead temperature is 92° C. Water (30.7 kg) is charged 1.4 hours into the strip. The final overhead temperature is about 97° C. and the final bottoms temperature is about 108° C. DEK (4.95 kg) is added to the stripped reactor contents, followed by 14 kg of water and 7.55 kg of 25% NaOH, and the mixture is agitated for 30 minutes at 70°–80° C. After a 30-minute settling time, the aqueous and organic phases are separated from each other. The aqueous phase is charged back to the workup reactor and stripped of DEK with a final bottoms temperature of about 95° C. and a final overhead temperature of about 95° C. A 2.0 kg water charge is added along with 5.15 kg of toluene. This mixture is agitated for 20 minutes and allowed to settle overnight with 60° C. tempered water in the jacket. The phases are then separated. The aqueous phase is washed two more times with toluene (the first time with 5.1 kg, the second time with 4.95 kg) each time followed by a phase separation. The product is recovered as a water solution of sodium (±)-2-(6-methoxy-2-naphthyl)propionate.

EXAMPLE 95

Preparation of 6-Methoxy-2- Vinylnaphthalene

The 20-gallon jacketed stainless steel reactor is charged with a 12.5 kg of ACN, 12.5 kg of methyl isobutyl ketone (MIBK), and 12.45 kg of BMN produced as in Example 7 hereof, 4.6 g of $PdCl_2$, and 50.9 g of NMDP. The reactor is pressured and vented three times with 50 psig nitrogen. Then 6.8 kg of TEA is charged. The agitator is set at 160 rpm and the reactor is pressured and vented with 50 psig nitrogen. The agitator is set to 415 rpm, the reactor is pressured to 100 psig with ethylene, and heated with tempered water on the jacket. The reaction temperature ranges from 94° to 100° C., while the pressure varies from 388 to 432 psig. The total reaction time is 2.6 hours, but the reaction reaches about 99% conversion in about 1.8 hours. The reactor is cooled and the ethylene pressure is vented. After standing for about 16 hours with the agitator in operation, the reactor is heated to approximately 60° C. and the reactor contents are transferred to the 30-gallon glass-lined workup reactor. The 20-gallon reactor is charged with 12.4 kg of MIBK, which is then heated to about 60° C. and also transferred to workup reactor.

Workup of 6-Methoxy-2- Vinylnaphthalene

The crude MVN solution is stripped at 150 mm Hg to remove the ACN. The total strip time is 3.3 hours with a maximum bottoms temperature of about 76° C. A reflux ratio of 50 is used to line out the column. After the column stabilizes, the reflux ratio is reduced to five. This reflux ratio is maintained for 45 minutes and then reduced to three for 30 minutes. The reflux ratio is set at two for the next 55 minutes before finally switching to zero reflux for the last 25 minutes.

After cooling to 47° C., 9.4 kg of 25% NaOH is charged to the stripped mixture. The temperature drops with the addition of the caustic. The reactor is agitated for 15 minutes and then the agitator is shut off and the aqueous phase is allowed to settle for 30 minutes. The phases are separated, and a 1.05 kg water wash is charged to the organic phase and mixed therewith for 20 minutes. This is allowed to settle for 80 minutes and the aqueous phase is cut from the bottom of the reactor.

The TEA strip pressure is initially 150 mm Hg and is lowered throughout the strip to a final value of 70 mm Hg. The total strip time is 4.25 hours with a maximum bottoms temperature of about 78° C. The column is started up with a zero reflux ratio for the first 35 minutes of operation. The reflux ratio is then set at five and held there for 25 minutes. The reflux ratio is decreased to two for the final 3.25 hours of the strip. To the stripped product mixture is charged 8.1 kg of THF and the resultant MVN solution is filtered through a ten micron bag filter and a one micron cartridge filter. An additional 4.05 kg of THF is charged to the workup reactor and this is also filtered.

Hydrocarboxylation of 6-Methoxy-2-Vinylnaphthalene

The MVN solution is transferred to the above hydrocarboxylation reactor. To this are charged 4.3 g of $PdCl_2$ and 9.8 g of CuCl$_2$. The reactor is purged once with 50 psig nitrogen. The agitator is set to 118 rpm and 3.95 kg of 10% HCl is charged. The reactor is pressured to 80 psig with nitrogen and vented twice (agitating during pressurization, no agitation during the vent). A solution of 47.6 g NMDP in 248 g DEK is charged. The agitator speed is set at 401 rpm and the reactor is pressured and vented three times with 50 psig CO (agitating during pressurization, no agitation during the vent). The reactor is then pressured to 276 psig with CO and heated to 75° C. The reactor temperature varies from about 72° to about 80° C. and the pressure range is about 334 to 355 psig. The reaction is shutdown after 8.8 hours.

Product Workup

The (±)-2-(6-methoxy-2-naphthyl)propionic acid solution is charged to a workup reactor and neutralized with 2.0 kg of 25% NaOH. THF is stripped at atmospheric pressure over 20 minutes. The final bottoms temperature is about 79° C. and the final overhead temperature is about 77° C. The stripped mixture is cooled to 60° C. and to this are charged 14.0 kg of water and 8.0 kg of caustic. The mixture is agitated for 30 minutes at 75° C. The agitator is shut off and the contents of the reactor are allowed to settle for 30 minutes. The phases are separated. The aqueous solution is charged back to the reactor and left agitating for about 16 hours. The aqueous solution is then stripped at atmospheric pressure for 1.5 hours. The aqueous phase in the column is cut back to the reactor. One more strip is done using steam on the jacket. Additional distillate is drained from the column following the strip. The final bottoms temperature for the strip is about 101° C. and the final overhead temperature is about 100° C. A 5.05 kg charge of toluene is added to stripped product mixture, and the mixture is agitated for 20 minutes at 68° C. then allowed to settle for 30 minutes. The phases are cut to give an amber-orange aqueous solution and a dark-green organic solution. The aqueous solution is washed with 5.0 kg of toluene, giving a reddish-purple clear aqueous solution and a cloudy olive-green organic solution. The third toluene wash (5.05 kg, 71° C.) produces a clear purple aqueous solution and a cloudy yellow organic solution.

EXAMPLE 96

The procedure of Example 95 is repeated substantially as described with the following principal changes:

The initial charge to the first reactor is 12.4 kg of ACN, 12.65 kg of DEK, 12.45 kg of BMN made as in Example 7 hereof, 4.6 g of PdCl$_2$, and 51 g of NMDP. The second charge is 6.17 kg TEA. This 2.5-hour vinylation reaction is conducted at 88°–99° C. and 318–458 psig.

The ACN distillation in the MVN workup is at 150 mm Hg and involves a total strip time of 5.25 hours with a maximum bottoms temperature of 71.8° C. The TEA strip pressure is initially 150 mm Hg and is lowered throughout the 4-hour strip to a final value of 90 mm Hg.

The hydrocarboxylation solvent is a mixture of residual DEK and about 12 kg of added THF. The other components charged are 4.1 g of PdCl$_2$, 9.2 g of CuCl$_2$, 3.65 kg of 10% HCl, 44.7 g of NMDP in 222 g of DEK. The hydrocarboxylation reaction runs for 6.6 hours, with temperatures in the range of 74° to 77° C. and pressures in the range of 333 to 358 psig.

As in Example 95, the crude (±)-2-(6-methoxy-2-naphthyl)propionic acid is converted to sodium (±)-2-(6-methoxy-2-naphthyl)propionate, stripped of THF, and washed three times, each time with 5 kg of toluene, to yield an aqueous solution of sodium (±)-2-(6-methoxy-2-naphthyl)propionate.

EXAMPLE 97

The procedure of Example 95 is repeated substantially as described with the following principal changes:

The initial charge to the first reactor is 12.55 kg of ACN, 12.5 kg of MIBK, 12.5 kg of BMN made as in Example 7 hereof, 4.6 g of PdCl$_2$, and 51 g of NMDP. The second charge is 6.19 kg TEA. This 2.7-hour vinylation reaction is conducted at 88°–97° C. and 371–441 psig.

The ACN distillation in the MVN workup is at 150 mm Hg and involves a total strip time of 3.8 hours with a maximum bottoms temperature of 71° C. The TEA strip pressure is initially 150 mm Hg and is lowered throughout the 5.3-hour strip to a final value of 70 mm Hg.

The hydrocarboxylation solvent is a mixture of residual MIBK and about 12 kg of added THF. The other components charged are 4.6 g of PdCl$_2$, 9.5 g of CuCl$_2$, 3.85 kg of 10% HCl, 47 g of NMDP in 226 g of DEK. The hydrocarboxylation reaction is conducted for 7 hours, with temperatures in the range of 72° to 77° C. and pressures in the range of 333 to 357 psig.

As in Example 95, the crude (±)-2-(6-methoxy-2-naphthyl)propionic acid is converted to sodium (±)-2-(6-methoxy-2-naphthyl)propionate, stripped of THF, and washed three times, each time with 5 kg of toluene, to yield an aqueous solution of sodium (±)-2-(6-methoxy-2-naphthyl)propionate.

In producing 6-methoxy-2-vinylnaphthalene (MVN) from 2-bromo-6-methoxynaphthalene (BMN) by reaction with ethylene, using a palladium (II) salt such as PdCl$_2$ and neomenthyldiphenylphosphine (NMDP) as catalyst or catalyst precursors, the preferred reaction medium is a mixture comprising a C$_4$–C$_8$ ketone (especially diethyl ketone) and a C$_4$–C$_9$ trialkyl amine (especially triethylamine). This reaction medium preferably contains a reaction accelerating amount of water in the range of about 1 to about 3.5 weight percent of the total weight of the reaction mixture. The BMN:Pd:NMDP mole ratio is preferably in the range of about 1000:3000:1:2–10, respectively. (e.g., a BMN:Pd:NMP mole ratio of 2000:1:6), the mol ratio of amine:BMN is preferably in the range of 1–2:1 respectively, the mol ratio of ketone:amine is preferably in the range of 1.0–4.0:1 respectively, the reaction temperature is preferably in the range of about 80° to about 110° C. (e.g., about 95° C.), and the pressure of the ethylene used is preferably in the range of about 400 to about 1000 psig (e.g., about 420 psig). Under these conditions, reaction is usually complete within the range of about 2 to about 6 hours. Since the reaction tends to be exothermic, it is desirable to utilize reactors equipped with internal cooling coils, cooling jackets or other highly effective cooling means to ensure suitable temperature control. Laboratory experiments have indicated that in the reaction of BMN with ethylene using PdCl$_2$ and NMDP at 95° C. and 420 psig ethylene, as agitator speeds increase from 300 to 1500 rpm, reaction times to completion decrease by almost two hours. In addition, such experiment's have indicated that (i) at a BMN:Pd:NMP mole ratio of 2000:1:6, MVN yields are higher and the amount of solid by-products formed is lower, when using BMN concentrations at the lower end of the range of 20 to 35 wt % than at the higher end of the range; and (ii) maximum rate of reaction is achieved at about 3 wt % water when operating at 95° C., 420 psig ethylene, BMN:Pd:NMP mole ratio of 2000:1:6, and at 30 wt % BMN concentration. The reaction mixture formed in this manner contains amine-hydrobromide salt together with the desired MVN.

When it is desired to convert the MVN to (±)-2-(6-methoxy-2-naphthyl)propionic acid via a hydrocarboxylation reaction, it is important to remove the amine from the reaction mixture. This is preferably accomplished by mixing a concentrated (e.g., 23–27 wt %, most preferably 25 wt %) aqueous sodium hydroxide solution with the reaction mixture to liberate the amine. Preferably, the aqueous solution of sodium hydroxide is used in an amount that results in formation of a sodium bromide solution containing at least about 30 wt % (more preferably about 40 to 50 wt %) of sodium bromide, as the ensuing phase separation is made easier when the aqueous phase has the higher densities of such concentrated sodium bromide solutions. In addition, less of the ketone solvent and amine are soluble in aqueous phases having such higher sodium bromide concentrations, and thus solvent losses are thereby reduced. Temperatures during this sodium hydroxide treatment will typically be in the range of about 40° to about 70° C., and agitation periods in the range of about 5 to about 15 minutes will normally suffice. After mixing, the resulting mixture is allowed or caused to separate into the organic and aqueous phases, usually by allowing the mixture to stand in a quiescent state. The phases tend to separate quickly, e.g., in as little as 15 minutes. Moreover the phase interface is distinct and easy to detect since oligomeric coproducts tend to float on top of such a concentrated aqueous phase. Then the phases are separated from each other, for example by decantation or, more usually, by draining off the lower aqueous layer.

Next, substantially all of the amine is distilled from the remainder of the organic phase under low temperature and pressure conditions that suppress thermal oligomerization of the MVN contained in the residual liquid phase. Preferably, liquid makeup solvent (preferably an ether such as tetrahydrofuran) is mixed with the liquid mixture during or after the distillation of the amine.

In conducting the hydrocarboxylation of MVN, dilute aqueous HCl (e.g., 10% aqueous HCl) in an amount supplying about four mols of water per mol of the MVN and an HCl:MVN mole ratio of about 0.15 to about 0.27, more preferably about 0.18 to about 0.22, is typically employed. Preferably, the hydrocarboxylation process is conducted in the presence of a reaction-promoting catalytic quantity of PdCl$_2$ and NMDP, with or without the copresence of CuCl$_2$. Temperatures for the reaction in the range of about 25°–100° C. are preferable. The partial pressure of carbon monoxide in the reaction vessel is at least about 1 atmosphere (0 psig) at ambient temperature (or the temperature at which the vessel is charged). Preferred is a pressure from 0 to about 1000 psig at the reaction temperature.

Example 98 illustrates a preferred overall procedure for producing (±)-2-(6-methoxy-2-naphthyl)propionic acid on a large (1000 gallon) scale using fresh diethyl ketone (DEK) as a solvent/diluent in the process.

EXAMPLE 98

Preparation of 6-Methoxy-2- Vinylnaphthalene

To a 1000-gallon reactor are charged 750 kg of BMN made as in Example 7 hereof, 1305 kg of DEK, 368 kg of TEA, 0.3 kg of PdCl$_2$, 3.1 kg of NMDP, and 37 kg of water. The reactor is sealed, pressured to 100 psig with ethylene and the reactor temperature is adjusted to 95° C. The reactor is then pressured to 425–450 psig with ethylene and held at this pressure until the uptake of ethylene is completed. The reactor is cooled to 60° C. and excess ethylene is vented from the reactor. The reaction typically takes 4–6 hours to go to completion and typically gives a >95% BMN conversion and a MVN yield of 85–95%.

To the reaction product is added 557 kg of a 25 wt % aqueous sodium hydroxide solution. The mixture is stirred for 15 minutes at 50°–60° C. and then allowed to stand for 15 minutes. The bottom aqueous solution is drained from the vessel. The organic phase is then subjected to distillation at pressures in the range of 200 mm Hg to 300 mm Hg to distill off TEA to a level at which the weight ratio of TEA:MVN is less than 0.016. After adding THF to the residual organic phase (distilland or pot residue) to form a mixture in which the THF:DEK weight ratio is approximately 1:1, this mixture is filtered to remove solids (palladium catalyst residues and oligomeric or dimeric coproduct).

Hydrocarboxylation of 6-Methoxy-2-Vinylnaphthalene

Charged to a 1000-gallon reactor are the filtered THF-DEK-MVN solution produced in the above procedure containing 550 kg of MVN, 825 kg of DEK, and 825 kg of THF, followed by 0.3 kg of PdCl$_2$, 0.64 kg of CuCl$_2$, 3.1 kg of NMDP, and 200 kg of 10 wt % HCl. The reactor is then pressured to 100 psig with carbon monoxide and the reactor temperature is adjusted to 70° C. The reactor is then pressured to 360 psig with carbon monoxide and held at this pressure until the uptake of carbon monoxide is completed. The reactor is then cooled and the pressure is vented. The reaction typically takes 4–8 hours to go to completion with >95% MVN conversion and a yield of (±)-2-(6-methoxy-2-naphthyl)propionic acid of approximately 90%.

The THF is distilled from the reaction mixture at atmospheric pressure. Aqueous sodium hydroxide (25%) is added to the reactor to convert the (±)-2-(6-methoxy-2-naphthyl) propionic acid to sodium (±)-2-(6-methoxy-2-naphthyl) propionate. The resultant aqueous phase is separated from the organic phase which is composed mainly of DEK and impurities. The residual organics (DEK) are distilled from the aqueous sodium (±)-2-(6-methoxy-2-naphthyl) propionate phase at atmospheric pressure. The sodium (±)-2-(6-methoxy-2-naphthyl)propionate solution is desirably a 10–35 wt % solution, and if necessary, the concentration is adjusted to fall in this range by removal or addition of water. The aqueous sodium (±)-2-(6-methoxy-2-naphthyl) propionate phase is then washed with toluene to remove neutral impurities. Typically one to three toluene washes are used. A suitable temperature, typically 60°–80° C., is maintained to prevent the sodium (±)-2-(6-methoxy-2-naphthyl) propionate from precipitating. The sodium (±)-2-(6-methoxy-2-naphthyl)propionate solution is then acidified with sulfuric acid in the presence of toluene at about 97° C. The aqueous phase is cut from the bottom of the reactor and the toluene solution of (±)-2-(6-methoxy-2-naphthyl) propionic acid is washed with water (typically twice) at about 95° C. to remove residual acid. (±)-2-(6-Methoxy-2-naphthyl)propionic acid is then crystallized from the toluene solution of (±)-2-(6-methoxy-2-naphthyl)propionic acid.

Example 99 illustrates a preferred overall procedure for producing (±)-2-(6-methoxy-2-naphthyl)propionic acid on a large (1000 gallon) scale using recycle solvent (principally DEK and TEA) from a process conducted as in Example 98 above.

EXAMPLE 99

Preparation of 6-Methoxy-2-Vinylnaphthalene

To a 1000-gallon reactor are charged 750 kg of BMN made as in Example 7 hereof, a mixture of recycle solvent (DEK and TEA mixture containing typically about 1 wt % water) to give approximately 1305 kg of DEK and 368 kg of TEA. Catalyst consisting of 0.3 kg of $PdCl_2$, and 3.1 kg of NMDP is charged to the reactor. Fresh water is added (if necessary) to raise the water content of the reaction mixture to approximately 1.6 wt %. The reactor is then pressured to 100 psig with ethylene and the reactor temperature is adjusted to 95° C. The reactor is then pressured to 425–450 psig with ethylene and held at this pressure until the uptake of ethylene is completed. The reactor is cooled to 60° C. and excess ethylene is vented from the reactor. The reaction typically takes 4–6 hours to go to completion and typically gives a >95% BMN conversion and a MVN yield of 85–95%.

Workup and Hydrocarboxylation

Aqueous caustic (25% aqueous NaOH solution) is added to the reaction mixture containing MVN to liberate the TEA from the triethylamine hydrobromide salt. The aqueous layer is then separated from the organic layer, and the TEA is then recovered from the MVN, DEK, and TEA mixture by distillation. The distillate composed of DEK, TEA, and water is then recycled to the first step. THF is added to the distillation residue (distilland or pot residue) composed mainly of a MVN/DEK mixture plus some solids to produce a MVN mixture containing THF and DEK in a weight ratio of about 1:1 suitable for carboxylation. The resultant mixture is filtered to remove the solids therefrom. Fresh catalyst and aqueous HCl are added in proportions corresponding to those of Example 98 and the hydrocarboxylation reaction and product workup and recovery are carried out as in Example 98.

Examples 98 and 99 involve procedures and subject matter described in full in commonly-owned copending applications Ser. No. [Case PI-7022], filed (contemporaneously herewith) and Ser. No. [Case PI-7019], filed (contemporaneously herewith), the entire disclosures of which are incorporated herein by reference.

(±)-2-(6-Methoxy-2-naphthyl)propionic acid produced using any of the process embodiments of this invention can be resolved by various known procedures to form the chiral S(+)-2-(6-Methoxy-2-naphthyl)propionic acid, known as naproxen.

It is to be understood that the reactants and components referred to by chemical name or formula anywhere in the specification or claims hereof, whether referred to in the singular or plural, are identified as they exist prior to coming into contact with another substance referred to by chemical name or chemical type (e.g., another reactant, a solvent, or etc.). It matters not what preliminary chemical changes, transformations and/or reactions, if any, take place in the resulting mixture or solution or reaction medium as such changes, transformations and/or reactions are the natural result of bringing the specified reactants and/or components together under the conditions called for pursuant to this disclosure. Thus, the reactants and components are identified as ingredients to be brought together in connection with performing a desired chemical reaction or in forming a mixture to be used in conducting a desired reaction. Accordingly, even though the claims hereinafter may refer to substances, components and/or ingredients in the present tense ("comprises", "is", etc.), the reference is to the substance, component or ingredient as it existed at the time just before it was first contacted, blended or mixed with one or more other substances, components and/or ingredients in accordance with the present disclosure. Without limiting the generality of the foregoing, as an illustrative example, where a claim specifies that a catalyst is a palladium compound in combination with a ligand comprising trivalent phosphorus, this phraseology refers to the makeup of the substance before it is mixed with one or more other materials, and in addition, at the time the catalyst is actually performing its catalytic function it need not have its original makeup—instead whatever transformations, if any, that occur in situ as the catalytic reaction is conducted is what the claim is intended to cover. Likewise a Grignard reagent when formed in an ether solvent is regarded by chemists as being solvated by the ether, and conceivably the Grignard reagent may possibly also be in the form a fixed or transitory complex with the ether or conceivably, the Grignard reagent may possibly be in an equilibrium state between salvation and complexation with the ether while in solution. Thus, the fact that a substance, component or ingredient may have lost its original identity through a chemical reaction or transformation during the course of contacting, blending or mixing operations, if conducted in accordance with this disclosure and with the application of common sense and the ordinary skill of a chemist, is thus wholly immaterial for an accurate understanding and appreciation of the true meaning and substance of this disclosure and the claims thereof.

Each and every patent or other publication referred to in any portion of this specification is incorporated in toto into this disclosure by reference, as if fully set forth herein.

This invention is susceptible to considerable variation in its practice. Therefore the foregoing description is not intended to limit, and should not be construed as limiting, the invention to the particular exemplifications presented hereinabove. Rather, what is intended to be covered is as set forth in the ensuing claims and the equivalents thereof permitted as a matter of law.

We claim:

1. In a process for the production of (±)-2-(6-methoxy-2-naphthyl)propionic acid or precursor thereof from 2-bromo-6-methoxynaphthalene, the improvement which comprises using in the process a 2-bromo-6-methoxynaphthalene product formed by a process comprising:

a) methylating 6-bromo-2-naphthol with methyl bromide or methyl chloride, or both, in a halogen-free liquid solvent comprising at least about 40% by weight of one or more compounds of the formula RZ where R is a hydrogen atom or an alkyl group, and Z is a hydroxyl group or a cyanide group with the proviso that if Z is a cyanide group, R is an alkyl group, and in the presence of at least one strong base such that 2-bromo-6-methoxynaphthalene is formed.

2. A process according to claim 1 wherein the methylation in a) is conducted using methyl chloride.

3. A process according to claim 2 wherein said solvent is water, or at least one alcohol, or a mixture of water and at least one alcohol.

4. A process according to claim 2 wherein said solvent is 2-propanol, or a mixture 2-propanol and water.

5. A process according to claim 2 wherein said solvent is at least 98% by weight of at least one alcohol, and wherein the strong base is formed by mixing at least one alkali metal oxide or hydroxide with at least one alcohol.

6. A process according to claim 5 wherein the alkali metal of said oxide or hydroxide is sodium or potassium, or both, and the 2-bromo-6-methoxynaphthalene so formed is recovered and purified by a procedure which comprises:

1) distilling off solvent to leave a hot molten residue;
2) washing the residue while molten with water to remove alkali metal chloride by-product and water-soluble impurities, if any, from the residue;

3) distilling 2-bromo-6-methoxynaphthalene from the washed residue; and 4) crystallizing the 2-bromo-6-methoxynaphthalene from a liquid medium.

7. A process according to claim 5 wherein the alkali metal of said oxide or hydroxide is sodium or potassium, or both, and the 2-bromo-6-methoxynaphthalene so formed is recovered and purified by a procedure which comprises:

1) distilling off solvent to leave a hot molten residue;

2) washing the residue while molten with water to remove alkali metal chloride by-product and water-soluble impurities, if any, from the 2-bromo-6-methoxynaphthalene residue; and 3) crystallizing the 2-bromo-6-methoxynaphthalene from a liquid medium.

8. A process according to claim 2 wherein said solvent is at least substantially entirely composed of 2-propanol, and wherein the strong base is formed by mixing sodium hydroxide and/or potassium hydroxide with 2-propanol.

9. A process according to claim 8 wherein the 2-bromo-6-methoxynaphthalene so formed is recovered and purified by a procedure which comprises:

1) distilling off solvent to leave a hot molten residue;

2) washing the residue while molten with water to remove alkali metal chloride by-product and water-soluble impurities, if any, from the residue;

3) distilling 2-bromo-6-methoxynaphthalene from the washed residue; and 4) crystallizing the 2-bromo-6-methoxynaphthalene from a liquid medium.

10. A process according to claim 9 wherein said crystallization is conducted in 2-propanol.

11. In a process for the production of (±)-2-(6-methoxy-2-naphthyl)propionic acid or precursor thereof from 2-bromo-6-methoxynaphthalene, the improvement which comprises using in the process a 2-bromo-6-methoxynaphthalene product formed by a process comprising:

A) reacting 1,6-dibromo-2-naphthol with hydrogen or a precursor compound that generates nascent hydrogen in the medium of the reaction, in a halogen-containing liquid solvent comprising at least about 50% by weight of (a) at least one liquid organic halide solvent in which the halogen content has an atomic number of 35 or less or (b) a mixture of water and at least one such liquid organic halide solvent, and in the presence of catalytically effective amounts of (i) a tungsten carbide-based catalyst, and (ii) at least one phase transfer catalyst, such that 6-bromo-2-naphthol is formed;

B) separating 6-bromo-2-naphthol so formed from said organic halide solvent so that the 6-bromo-2-naphthol is at least substantially completely free from any halogen-containing impurity content;

C) methylating 6-bromo-2-naphthol from B) with methyl bromide or methyl chloride, or both, in a halogen-free liquid solvent comprising at least 40% by weight of one or more compounds of the formula RZ where R is a hydrogen atom or an alkyl group, and Z is a hydroxyl group or a cyanide group with the proviso that if Z is a cyanide group, R is an alkyl group, and in the presence of at least one strong base such that 2-bromo-6-methoxynaphthalene is formed.

12. A process according to claim 11 wherein A) is conducted in the presence at the start of the reaction of a small, reaction-initiating amount of hydrobromic acid or hydrogen bromide, and wherein in A) hydrogen bromide is substantially continuously purged from the reaction mixture substantially as soon as it is formed.

13. A process according to claim 11 wherein the methylation in C) is conducted using methyl chloride.

14. A process according to claim 13 wherein said halogen-containing solvent is ethylene dichloride, and wherein the separation of 6-bromo-2-naphthol from the ethylene dichloride is effected by distilling off most of the ethylene dichloride and then adding water and distilling off the remainder of the ethylene dichloride azeotropically with water.

15. A process according to claim 13 wherein the liquid phase in A) contains hydrogen bromide during at least substantially the entire reaction period of A).

16. A process according to claim 13 wherein said halogen-containing solvent is ethylene dichloride, wherein the liquid phase in A) contains hydrogen bromide during at least substantially the entire reaction period of A), and wherein the separation of 6-bromo-2-naphthol from the ethylene dichloride is effected by distilling off most of the ethylene dichloride and then adding water and distilling off the remainder of the ethylene dichloride azeotropically with water.

17. A process according to claim 13 wherein said halogen-free solvent is water, or at least one alcohol, a mixture of water and at least one alcohol.

18. A process according to claim 16 wherein said halogen-free solvent is water, or at least one alcohol, or a mixture of water and at least one alcohol.

19. A process according to claim 16 wherein said halogen-free solvent is 2-propanol, or a mixture of 2-propanol and water.

20. A process according to claim 16 wherein said halogen-free solvent is at least 98% by weight of at least one alcohol, and wherein the strong base is formed by mixing at least one alkali metal oxide or hydroxide with at least one alcohol.

21. A process according to claim 20 wherein the alkali metal of said oxide or hydroxide is sodium or potassium, or both, and the so formed 2-bromo-6-methoxynaphthalene is recovered and purified by a procedure which comprises:

1) distilling off solvent to leave a hot molten residue;

2) washing the residue while molten with water to remove alkali metal chloride by-product, remains of phase transfer catalyst, and other water-soluble impurities, if any, from the residue;

3) distilling 2-bromo-6-methoxynaphthalene from the washed residue; and 4) crystallizing the 2-bromo-6-methoxynaphthalene from a liquid medium.

22. A process according to claim 20 wherein the alkali metal of said oxide or hydroxide is sodium or potassium, or both, and the so formed 2-bromo-6-methoxynaphthalene is recovered and purified by a procedure which comprises:

1) distilling off solvent to leave a hot molten residue;

2) washing the residue while molten with water to remove alkali metal chloride by-product, remains of phase transfer catalyst, and other water-soluble impurities, if any, from the 2-bromo-6-methoxynaphthalene residue; and 3) crystallizing the 2-bromo-6-methoxynaphthalene from a liquid medium.

23. A process according to claim 16 wherein said halogen-free solvent is at least substantially entirely composed of 2-propanol, and wherein the strong base is formed by mixing sodium hydroxide with 2-propanol.

24. A process according to claim 23 wherein the so formed 2-bromo-6-methoxynaphthalene is recovered and purified by a procedure which comprises:

1) distilling off solvent to leave a hot molten residue;

2) washing the residue while molten with water to remove sodium chloride by-product, remains of phase transfer catalyst, and other water-soluble impurities, if any, from the residue;

3) distilling 2-bromo-6-methoxynaphthalene from the washed residue; and 4) crystallizing the 2-bromo-6-methoxynaphthalene from a liquid medium.

25. A process according to claim 24 wherein said crystallization is conducted in 2-propanol.

26. A process according to claim 11 wherein A) is conducted in the presence at the start of the reaction of a small, reaction-initiating amount of hydrobromic acid or hydrogen bromide, wherein in A) hydrogen bromide is substantially continuously purged from the reaction mixture substantially as soon as it is formed, and wherein the methylation in C) is conducted using methyl chloride.

27. A process according to claim 26 wherein said halogen-containing solvent is ethylene dichloride, and wherein the separation of 6-bromo-2-naphthol from the ethylene dichloride is effected by distilling off most of the ethylene dichloride and then adding water and distilling off the remainder of the ethylene dichloride azeotropically with water.

28. A process according to claim 26 wherein the liquid phase in A) contains hydrogen bromide during at least substantially the entire reaction period of A).

29. A process according to claim 26 wherein said halogen-containing solvent is ethylene dichloride, wherein the liquid phase in A) contains hydrogen bromide during at least substantially the entire reaction period of A), and wherein the separation of 6-bromo-2-naphthol from the ethylene dichloride is effected by distilling off most of the ethylene dichloride and then adding water and distilling off the remainder of the ethylene dichloride azeotropically with water.

30. A process according to claim 26 wherein said halogen-free solvent is water, or at least one alcohol, or a mixture of water and at least one alcohol.

31. A process according to claim 29 wherein said halogen-free solvent is water, or at least one alcohol, or a mixture of water and at least one alcohol.

32. A process according to claim 29 wherein said halogen-free solvent is 2-propanol, or a mixture of 2-propanol and water.

33. A process according to claim 29 wherein said halogen-free solvent is at least 98% by weight of at least one alcohol, and wherein the strong base is formed by mixing at least one alkali metal oxide or hydroxide with at least one alcohol.

34. A process according to claim 33 wherein the alkali metal of said oxide or hydroxide is sodium or potassium, or both, and the so formed 2-bromo-6-methoxynaphthalene is recovered and purified by a procedure which comprises:

1) distilling off solvent to leave a hot molten residue;

2) washing the residue while molten with water to remove alkali metal chloride by-product, remains of phase transfer catalyst, and other water-soluble impurities, if any, from the residue;

3) distilling 2-bromo-6-methoxynaphthalene from the washed residue; and 4) crystallizing the 2-bromo-6-methoxynaphthalene from a liquid medium.

35. A process according to claim 33 wherein the alkali metal of said oxide or hydroxide is sodium or potassium, or both, and the so formed 2-bromo-6-methoxynaphthalene is recovered and purified by a procedure which comprises:

1) distilling off solvent to leave a hot molten residue;

2) washing the residue while molten with water to remove alkali metal chloride by-product, remains of phase transfer catalyst, and other water-soluble impurities, if any, from the 2-bromo-6-methoxynaphthalene residue; and 3) crystallizing the 2-bromo-6-methoxynaphthalene from a liquid medium.

36. A process according to claim 29 wherein said halogen-free solvent is at least substantially entirely composed of 2-propanol, and wherein the strong base is formed by mixing sodium hydroxide with 2-propanol.

37. A process according to claim 36 wherein the so formed 2-bromo-6-methoxynaphthalene is recovered and purified by a procedure which comprises:

1) distilling off solvent to leave a hot molten residue;

2) washing the residue while molten with water to remove sodium chloride by-product, remains of phase transfer catalyst, and other water-soluble impurities, if any, from the residue;

3) distilling 2-bromo-6-methoxynaphthalene from the washed residue; and 4) crystallizing the 2-bromo-6-methoxynaphthalene from a liquid medium.

38. A process according to claim 37 wherein said crystallization is conducted in 2-propanol.

39. A process which comprises:

a) methylating 6-bromo-2-naphthol with methyl bromide or methyl chloride, or both, in a halogen-free liquid solvent comprising at least about 40% by weight of one or more compounds of the formula RZ where R is a hydrogen atom or an alkyl group, and Z is a hydroxyl group or a cyanide group with the proviso that if Z is a cyanide group, R is an alkyl group, and in the presence of at least one strong base such that 2-bromo-6-methoxynaphthalene is formed; and b) converting 2-bromo-6-methoxynaphthalene from a) into a Grignard reagent by reaction with magnesium in a suitable essentially anhydrous liquid reaction medium in an essentially inert atmosphere.

40. A process according to claim 39 wherein the methylation in a) is conducted using methyl chloride.

41. A process according to claim 40 wherein said 6-bromo-2-naphthol is formed by a process comprising:

A) reacting 1,6-dibromo-2-naphthol with hydrogen or a precursor compound that generates nascent hydrogen in the medium of the reaction, in a halogen-containing liquid solvent comprising at least about 50% by weight of (a) at least one liquid organic halide solvent in which the halogen content has an atomic number of 35 or less or (b) a mixture of water and at least one such liquid organic halide solvent, and in the presence of catalytically effective amounts of (i) a tungsten carbide-based catalyst, and (ii) at least one phase transfer catalyst, such that 6-bromo-2-naphthol is formed; and B) separating 6-bromo-2-naphthol so formed from said organic halide solvent so that the 6-bromo-2-naphthol is at least substantially completely free from any halogen-containing impurity content.

42. A process according to claim 41 wherein A) is conducted in the presence at the start of the reaction of a small, reaction-initiating amount of hydrobromic acid or hydrogen bromide, and wherein in A) hydrogen bromide is substantially continuously purged from the reaction mixture substantially as soon as it is formed.

43. A process according to claim 39 further comprising converting Grignard reagent from b) into zinc-containing reagent selected from (i) bis(6-methoxy-2-naphthyl)zinc, (ii) (6-methoxy-2-naphthyl)zinc halide, or (iii) a mixture of (i) and (ii).

44. A process according to claim 43 further comprising converting at least a portion of said zinc-containing reagent into (±)-2-(6-methoxy-2-naphthyl)propionic acid by reaction with a lower alkyl 2-bromopropionate in an inert solvent until a lower alkyl 2-(6-methoxy-2-naphthyl) propionate is formed, and hydrolyzing the ester group of the lower alkyl 2-(6-methoxy-2-naphthyl)propionate to form 2-(6-methoxy-2-naphthyl)propionic acid.

45. A process according to claim 42 further comprising converting Grignard reagent from b) into zinc-containing reagent selected from (i) bis(6-methoxy-2-naphthyl)zinc, (ii) (6-methoxy-2-naphthyl)zinc halide, or (iii) a mixture of (i) and (ii).

46. A process according to claim 45 further comprising converting at least a portion of said zinc-containing reagent into (±)-2-(6-methoxy-2-naphthyl)propionic acid by reaction with a lower alkyl 2-bromopropionate in an inert solvent until a lower alkyl 2-(6-methoxy-2-naphthyl) propionate is formed, and hydrolyzing the ester group of the lower alkyl 2-(6-methoxy-2-naphthyl)propionate to form 2-(6-methoxy-2-naphthyl)propionic acid.

47. A process according to claim 39 further comprising converting Grignard reagent from b) into cadmium-containing reagent selected from (i) bis(6-methoxy-2-naphthyl)cadmium, (ii) (6methoxy-2-naphthyl)cadmium halide, or (iii) a mixture of (i) and (ii).

48. A process according to claim 47 further comprising converting at least a portion of said cadmium-containing reagent into (±)-2-(6-methoxy-2-naphthyl)propionic acid by reaction with a lower alkyl 2-bromopropionate in a suitable solvent until a lower alkyl 2-(6-methoxy-2-naphthyl) propionate is formed, and hydrolyzing the ester group of the lower alkyl 2-(6-methoxy-2-naphthyl)propionate to form 2-(6-methoxy-2-naphthyl)propionic acid.

49. A process according to claim 42 further comprising converting Grignard reagent from b) into cadmium-containing reagent selected from (i) bis(6-methoxy-2-naphthyl)cadmium, (ii)(6-methoxy-2-naphthyl)cadmium halide, or (iii) a mixture of (i) and (ii).

50. A process according to claim 49 further comprising converting at least a portion of said cadmium-containing reagent into (±)-2-(6-methoxy-2-naphthyl)propionic acid by reaction with a lower alkyl 2-bromopropionate in a suitable solvent until a lower alkyl 2-(6-methoxy-2-naphthyl) propionate is formed, and hydrolyzing the ester group of the lower alkyl 2-(6-methoxy-2-naphthyl)propionate to form 2-(6-methoxy-2-naphthyl)propionic acid.

51. A process according to claim 39 further comprising converting Grignard reagent from b) into (±)-2-(6-methoxy-2-naphthyl)propionic acid by reaction in a suitable liquid reaction medium with at least one light metal salt of 2-bromopropionic acid selected from the lithium, sodium, magnesium and calcium salts of 2-bromopropionic acid, and acidifying the product formed in this reaction.

52. A process according to claim 42 further comprising converting Grignard reagent from b) into (±)-2-(6-methoxy-2-naphthyl)propionic acid by reaction in a suitable liquid reaction medium with at least one light metal salt of 2-bromopropionic acid selected from the lithium, sodium, magnesium and calcium salts of 2-bromopropionic acid, and acidifying the product formed in this reaction.

53. A process according to claim 39 further comprising converting Grignard reagent from b) into (±)-2-(6-methoxy-2-naphthyl)propionic acid by reaction in a suitable liquid reaction medium with at least one mixed magnesium halide complex of 2-bromopropionic acid, and acidifying the product formed in this reaction.

54. A process according to claim 42 further comprising converting Grignard reagent from b) into (±)-2-(6-methoxy-2-naphthyl)propionic acid by reaction in a suitable liquid reaction medium with at least one mixed magnesium halide complex of 2-bromopropionic acid, and acidifying of the product formed in this reaction.

55. A process which comprises:
  a) methylating 6-bromo-2-naphthol with methyl bromide or methyl chloride, or both, in a halogen-free liquid solvent comprising at least about 40% by weight of one or more compounds of the formula RZ where R is a hydrogen atom or an alkyl group, and Z is a hydroxyl group or a cyanide group with the proviso that if Z is a cyanide group, R is an alkyl group, and in the presence of at least one strong base such that 2-bromo-6-methoxynaphthalene is formed; and
  b) converting 2-bromo-6-methoxynaphthalene from a) into 6-methoxy-2-naphthyllithium by reaction with lithium in a suitable essentially anhydrous liquid reaction medium in an essentially inert atmosphere.

56. A process according to claim 55 wherein the methylation in a) is conducted using methyl chloride.

57. A process according to claim 56 wherein said 6-bromo-2-naphthol is formed by a process comprising:
  A) reacting 1,6-dibromo-2-naphthol with hydrogen or a precursor compound that generates nascent hydrogen in the medium of the reaction, in a halogen-containing liquid solvent comprising at least about 50% by weight of (a) at least one liquid organic halide solvent in which the halogen content has an atomic number of 35 or less or (b) a mixture of water and at least one such liquid organic halide solvent, and in the presence of catalytically effective amounts of (i) a tungsten carbide-based catalyst, and (ii) at least one phase transfer catalyst, such that 6-bromo-2-naphthol is formed; and
  B) separating 6-bromo-2-naphthol so formed from said organic halide solvent so that the 6-bromo-2-naphthol is at least substantially completely free from any halogen-containing impurity content.

58. A process according to claim 57 wherein A) is conducted in the presence at the start of the reaction of a small, reaction-initiating amount of hydrobromic acid or hydrogen bromide, and wherein in A) hydrogen bromide is substantially continuously purged from the reaction mixture substantially as soon as it is formed.

59. A process according to claim 55 further comprising converting at least a portion of said 6-methoxy-2-naphthyllithium into 6-methoxy-2-naphthylcopper(I) by reaction with a cuprous halide in a suitable liquid reaction medium.

60. A process according to claim 59 further comprising converting at least a portion of said 6-methoxy-2-naphthylcopper(I) into (±)-2-(6-methoxy-2-naphthyl) propionic acid by reaction with a lower alkyl 2-bromopropionate in a suitable solvent until a lower alkyl 2-(6-methoxy-2-naphthyl)propionate is formed, and hydrolyzing the ester group of the lower alkyl 2-(6-methoxy-2-naphthyl)propionate to form 2-(6-methoxy-2-naphthyl) propionic acid.

61. A process according to claim 58 further comprising converting at least a portion of said 6-methoxy-2-naphthyllithium into 6-methoxy-2-naphthylcopper(I) by reaction with a cuprous halide in a suitable liquid reaction medium.

62. A process according to claim 61 further comprising converting at least a portion of said 6-methoxy-2-naphthylcopper(I) into (±)-2-(6-methoxy-2-naphthyl)propionic acid by reaction with a lower alkyl 2-bromopropionate in a suitable solvent until a lower alkyl 2-(6-methoxy-2-naphthyl)propionate is formed, and hydrolyzing the ester group of the lower alkyl 2-(6-methoxy-2-naphthyl)propionate to form 2-(6-methoxy-2-naphthyl)propionic acid.

63. A process which comprises:
   a) methylating 6-bromo-2-naphthol with methyl bromide or methyl chloride, or both, in a halogen-free liquid solvent comprising at least about 40% by weight of one or more compounds of the formula RZ where R is a hydrogen atom or an alkyl group, and Z is a hydroxyl group or a cyanide group with the proviso that if Z is a cyanide group, R is an alkyl group, and in the presence of at least one strong base such that 2-bromo-6-methoxynaphthalene is formed; and
   b) converting 2-bromo-6-methoxynaphthalene from a) into 6-methoxy-2-vinylnaphthalene by reaction with ethylene in the presence of a catalyst formed by addition to the reaction mixture or to a component used to form said reaction mixture of (i) palladium (0) and/or at least one of the salts of palladium having a valence of 0, 1 or 2, and (ii) at least one tri-substituted phosphine where two of the substituents are aryl groups and the third substituent is a cycloaliphatic group.

64. A process according to claim 63 wherein the methylation in a) is conducted using methyl chloride.

65. A process according to claim 64 wherein said 6-bromo-2-naphthol is formed by a process comprising:
   A) reacting 1,6-dibromo-2-naphthol with hydrogen or a precursor compound that generates nascent hydrogen in the medium of the reaction, in a halogen-containing liquid solvent comprising at least about 50% by weight of (a) at least one liquid organic halide solvent in which the halogen content has an atomic number of 35 or less or (b) a mixture of water and at least one such liquid organic halide solvent, and in the presence of catalytically effective amounts of (i) a tungsten carbide-based catalyst, and (ii) at least one phase transfer catalyst, such that 6-bromo-2-naphthol is formed; and
   B) separating 6-bromo-2-naphthol so formed from said organic halide solvent so that the 6-bromo-2-naphthol is at least substantially completely free from any halogen-containing impurity content.

66. A process according to claim 65 wherein A) is conducted in the presence at the start of the reaction of a small, reaction-initiating amount of hydrobromic acid or hydrogen bromide, and wherein in A) hydrogen bromide is substantially continuously purged from the reaction mixture substantially as soon as it is formed.

67. A process according to claim 63 wherein in b), ingredient (i) used in forming the catalyst is at least one palladium (II) salt, and the reaction of b) is performed in a suitable liquid reaction medium.

68. A process according to claim 67 wherein the liquid reaction medium used in c) is composed predominately of acetonitrile.

69. A process according to claim 63 wherein in b), ingredient (i) used in forming the catalyst is neomenthyldiphenylphosphine, and the reaction of b) is performed in a suitable liquid reaction medium.

70. A process according to claim 69 wherein the liquid reaction medium used in c) is composed predominately of acetonitrile.

71. A process according to claim 70 wherein in b), ingredient (i) used in forming the catalyst is palladium (II) chloride.

72. A process according to claim 66 wherein in b), ingredient (i) used in forming the catalyst is at least one palladium (II) salt, and the reaction of b) is performed in a suitable liquid reaction medium.

73. A process according to claim 72 wherein the liquid reaction medium used in b) is composed predominately of acetonitrile.

74. A process according to claim 66 wherein in b), ingredient (i) used in forming the catalyst is neomenthyldiphenylphosphine, and the reaction of b) is performed in a suitable liquid reaction medium.

75. A process according to claim 74 wherein the liquid reaction medium used in b) is composed predominately of acetonitrile.

76. A process according to claim 75 wherein in b), ingredient (i) used in forming the catalyst is palladium (II) chloride.

77. A process according to claim 63 further comprising converting 6-methoxy-2-vinylnaphthalene from b) into (±)-2-(6-methoxy-2-naphthyl)propionic acid by hydrocarboxylation with carbon monoxide and water in the presence of a catalyst formed by addition to the reaction mixture or to a component used to form said reaction mixture of at least the following ingredients: (i) palladium (0) and/or at least one of the salts of palladium having a valence of 0, 1 or 2, and (ii) at least one tri-substituted phosphine where two of the substituents are aryl groups the third substituent is a cycloaliphatic group.

78. A process according to claim 77 wherein ingredient (i) used in forming the catalyst is a Pd(II) salt.

79. A process according to claim 77 wherein ingredient (ii) used in forming the catalyst is neomenthyldiphenylphosphine.

80. A process according to claim 77 wherein at least one water-soluble copper(II) salt and hydrochloric acid and/or hydrogen chloride are also charged to the reaction system to enhance the reaction.

81. A process according to claim 77 wherein the reaction is performed in the presence of a suitable water-compatible polar co-solvent.

82. A process according to claim 81 wherein ingredient (ii) used in forming the catalyst is neomenthyldiphenylphosphine and wherein at least one water-soluble copper(II) salt and hydrochloric acid and/or hydrogen chloride are also charged to the reaction system to enhance the reaction.

83. A process according to claim 82 wherein ingredient (i) used in forming the catalyst is Pd(II) chloride and the copper(II) salt is a copper(II) halide.

84. A process according to claim 66 further comprising converting 6-methoxy-2-vinylnaphthalene from b) into (±)-2-(6-methoxy-2-naphthyl)propionic acid by hydrocarboxylation with carbon monoxide and water in the presence of a catalyst formed by addition to the reaction mixture or to a component used to form said reaction mixture of at least the following ingredients: (i) palladium (0) and/or at least one of the salts of palladium having a valence of 0, 1 or 2, and (ii) at least one tri-substituted phosphine where two of the substituents are aryl groups and the third substituent is a cycloaliphatic group.

85. A process according to claim 84 wherein ingredient (i) used in forming the catalyst is a Pd(II) salt.

86. A process according to claim 84 wherein ingredient (ii) used in forming the catalyst is neomenthyldiphenylphosphine.

87. A process according to claim 84 wherein at least one water-soluble copper(II) salt and hydrochloric acid and/or hydrogen chloride are also charged to the reaction system to enhance the reaction.

88. A process according to claim 84 wherein the reaction is performed in the presence of a suitable water-compatible polar co-solvent.

89. A process according to claim 88 wherein ingredient (ii) used in forming the catalyst is neomenthyldiphenylphosphine and wherein at least one water-soluble copper(II) salt and hydrochloric acid and/or hydrogen chloride are also charged to the reaction system to enhance the reaction.

90. A process according to claim 89 wherein ingredient (i) used in forming the catalyst is Pd(II) chloride and the copper(II) salt is a copper(II) halide.

* * * * *